United States Patent [19]
Kimura et al.

[11] Patent Number: 6,039,752
[45] Date of Patent: Mar. 21, 2000

[54] TREATING INSTRUMENT FOR OPERATION AND MEDICAL DEVICE USING THE TREATMENT DEVICE

[75] Inventors: Kenichi Kimura, Hachioji; Akira Shiga, Hidaka; Toshihiko Hashiguchi, Sagamihara; Eiji Murakami, Hachioji; Katsumi Sasaki, Tokyo, all of Japan

[73] Assignee: Olympus Optical Co., Ltd., Tokyo, Japan

[21] Appl. No.: 08/881,892

[22] Filed: Jun. 24, 1997

[30] Foreign Application Priority Data

Sep. 4, 1996 [JP] Japan ..................................... 8-234280
Jun. 6, 1997 [JP] Japan ..................................... 9-149037

[51] Int. Cl.⁷ .................................................. A61B 17/28
[52] U.S. Cl. ............................................................ 606/205
[58] Field of Search ..................................... 606/161, 205, 606/206

[56] References Cited

U.S. PATENT DOCUMENTS

| | | |
|---|---|---|
| 4,043,323 | 8/1977 | Komiya . |
| 4,091,539 | 5/1978 | Watanabe . |
| 5,160,343 | 11/1992 | Brancel et al. . |
| 5,174,300 | 12/1992 | Bales et al. ............................. 606/205 |
| 5,318,579 | 6/1994 | Chow ...................................... 606/205 |
| 5,342,390 | 8/1994 | Slater et al. ............................ 606/205 |
| 5,342,391 | 8/1994 | Foshee et al. .......................... 606/205 |
| 5,359,993 | 11/1994 | Slater et al. ............................ 606/205 |

FOREIGN PATENT DOCUMENTS

| | | |
|---|---|---|
| 0159453 A1 | 10/1985 | European Pat. Off. . |
| 3526821 A1 | 2/1987 | Germany . |
| 4428479 A1 | 2/1996 | Germany . |
| 4429812 A1 | 2/1996 | Germany . |
| 60-36293 | 8/1985 | Japan . |
| 4-246344 | 9/1992 | Japan . |
| WO 93/06977 | 4/1993 | WIPO . |

*Primary Examiner*—Michael Buiz
*Assistant Examiner*—Daphna Shai
*Attorney, Agent, or Firm*—Frishauf, Holtz, Goodman, Langer & Chick, P.C.

[57] ABSTRACT

A treating instrument for an operation includes an elastic ring for reducing a load on an operator's fingers which contact first and second rings of first and second handle elements. The elastic ring is provided on a section of at least one of the first and second rings which contacts the operator's fingers.

14 Claims, 18 Drawing Sheets

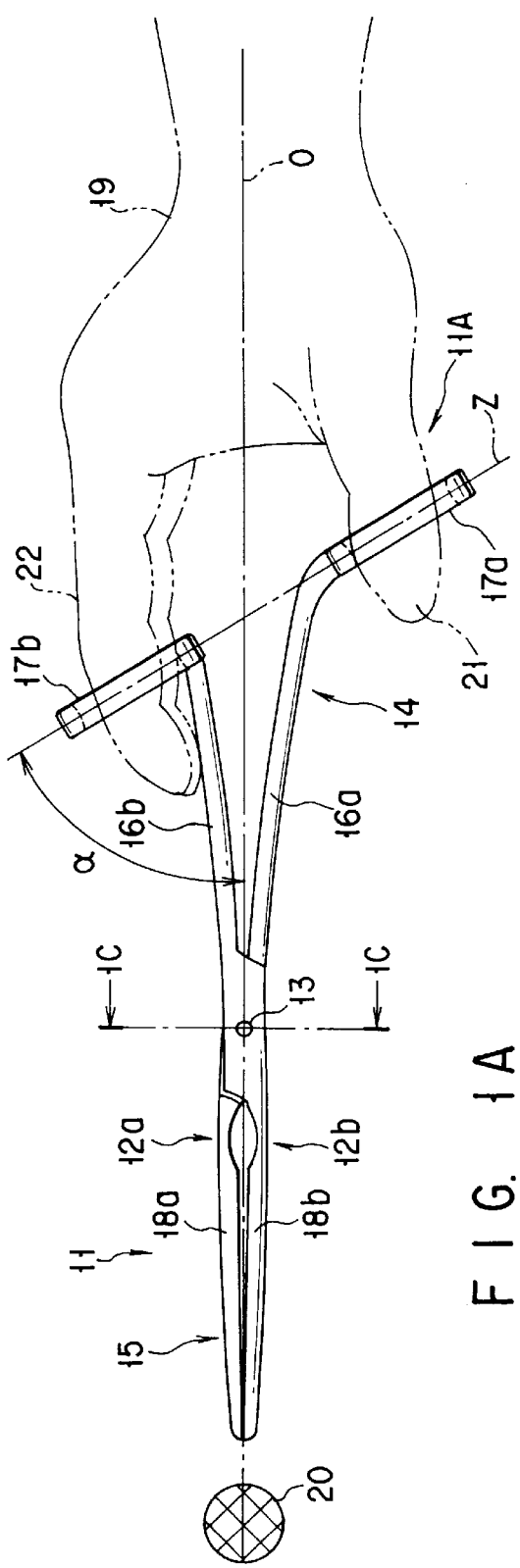
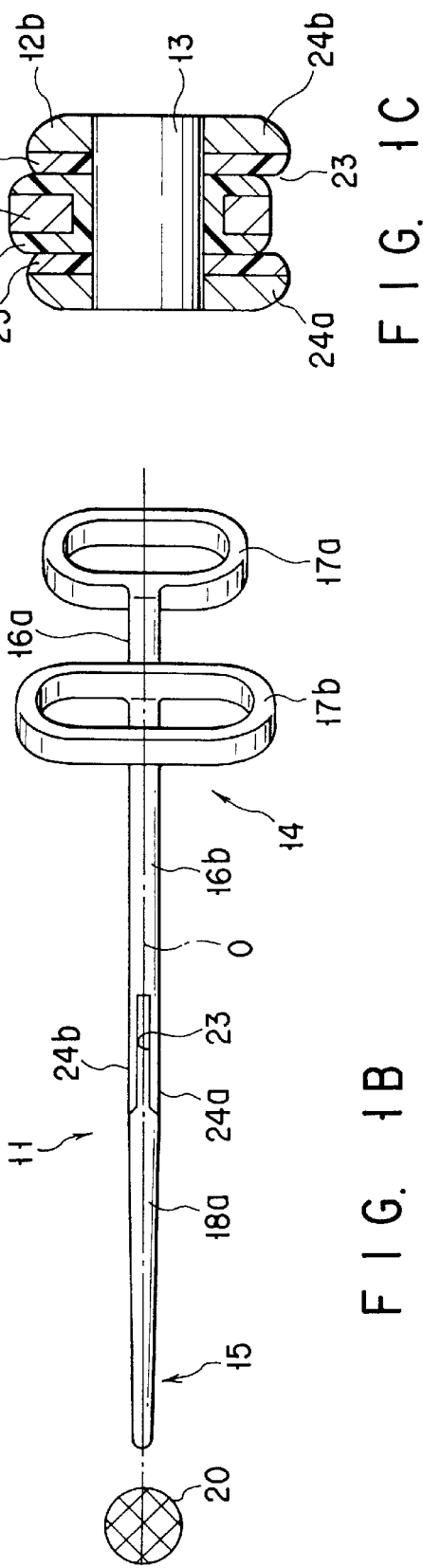
FIG. 1A  FIG. 1B  FIG. 1C

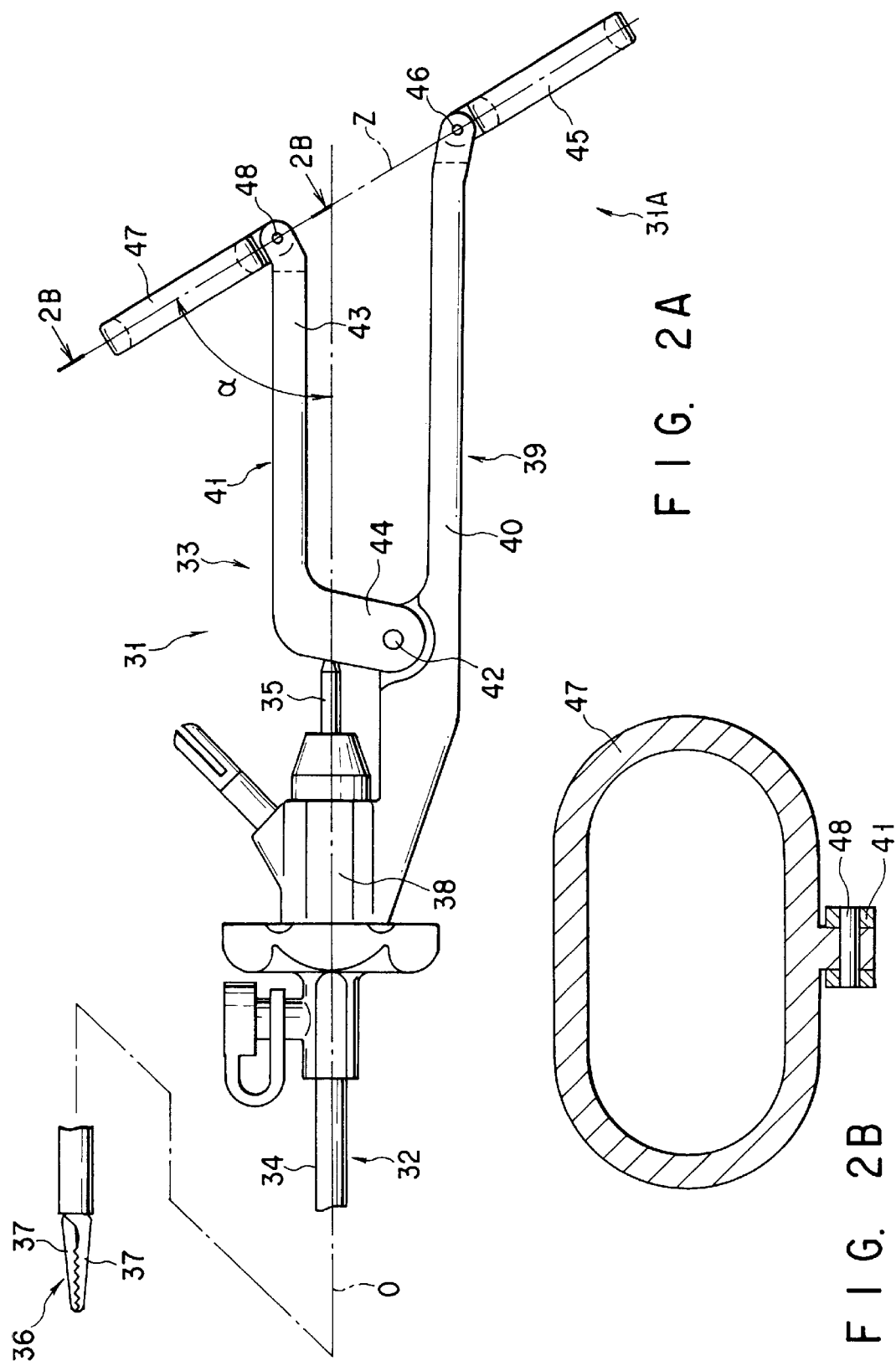

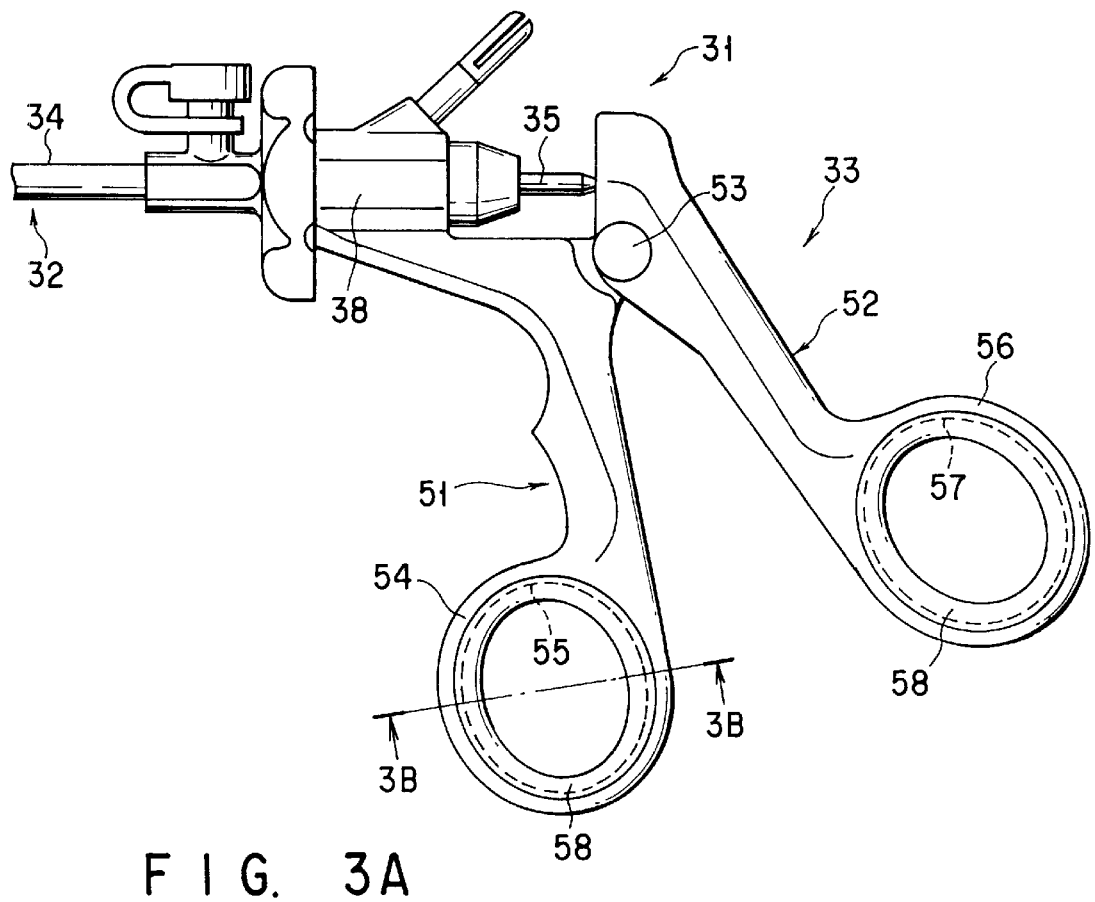
F I G. 3A
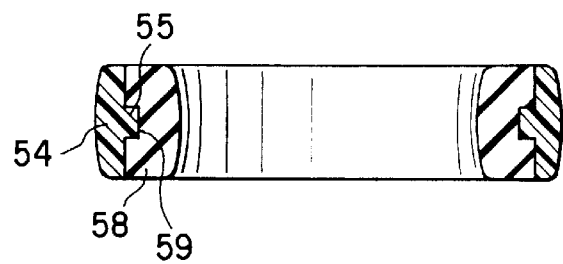
F I G. 3B

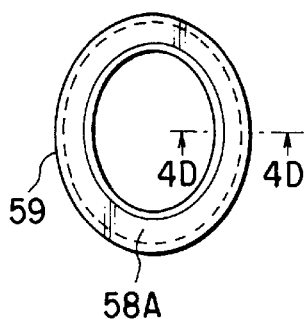
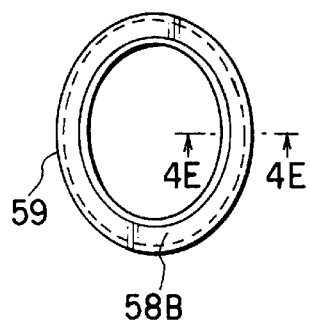
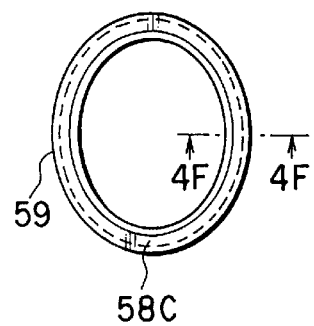
FIG. 4A     FIG. 4B     FIG. 4C
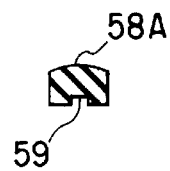
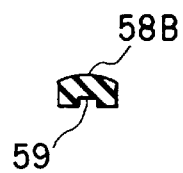
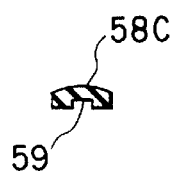
FIG. 4D     FIG. 4E     FIG. 4F
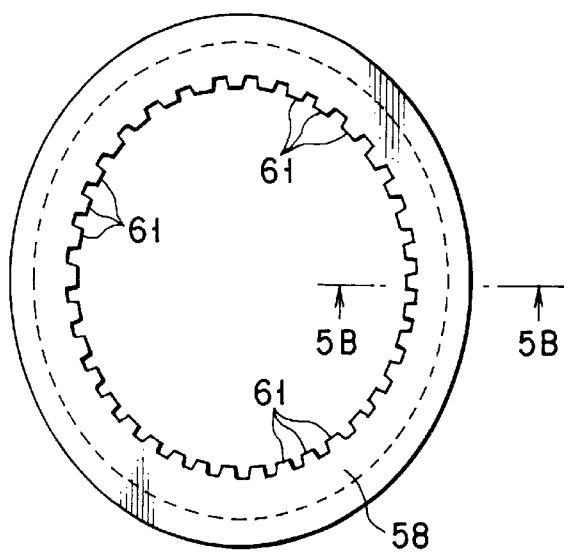
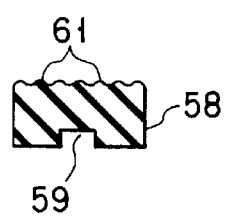
FIG. 5B
FIG. 5A

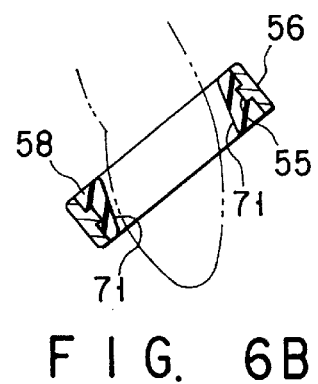
FIG. 6B
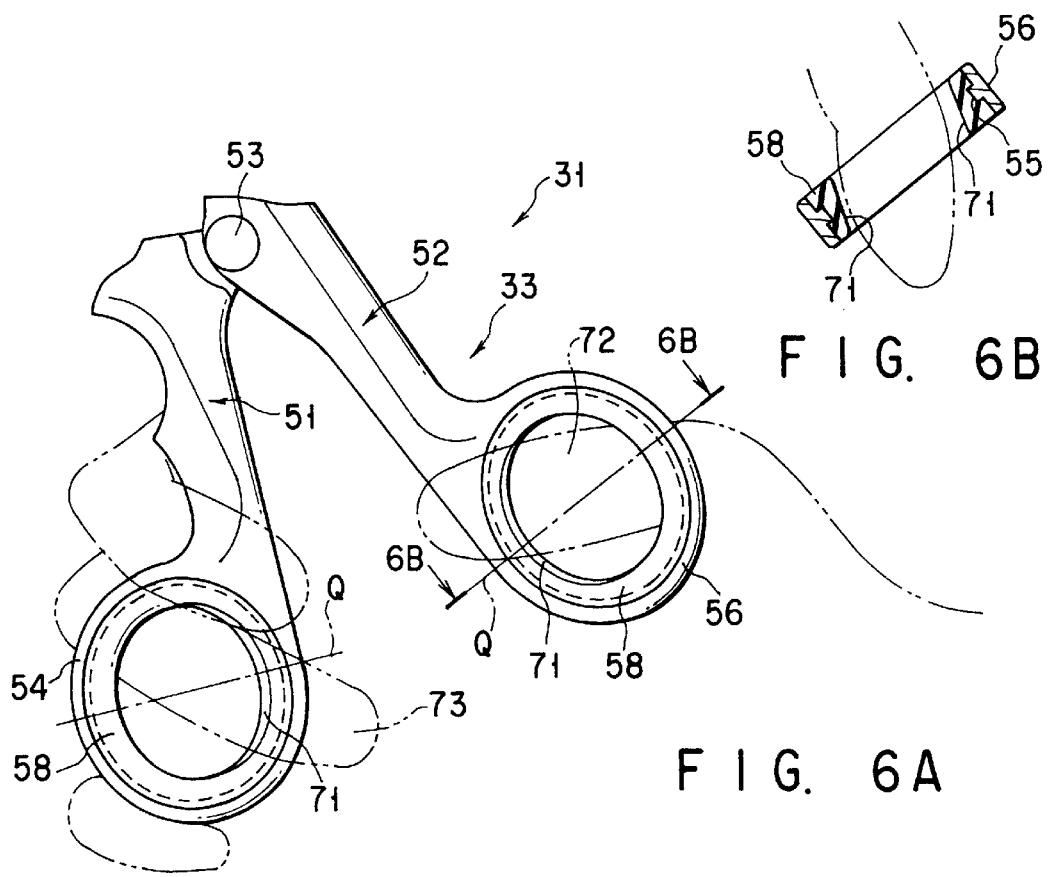
FIG. 6A
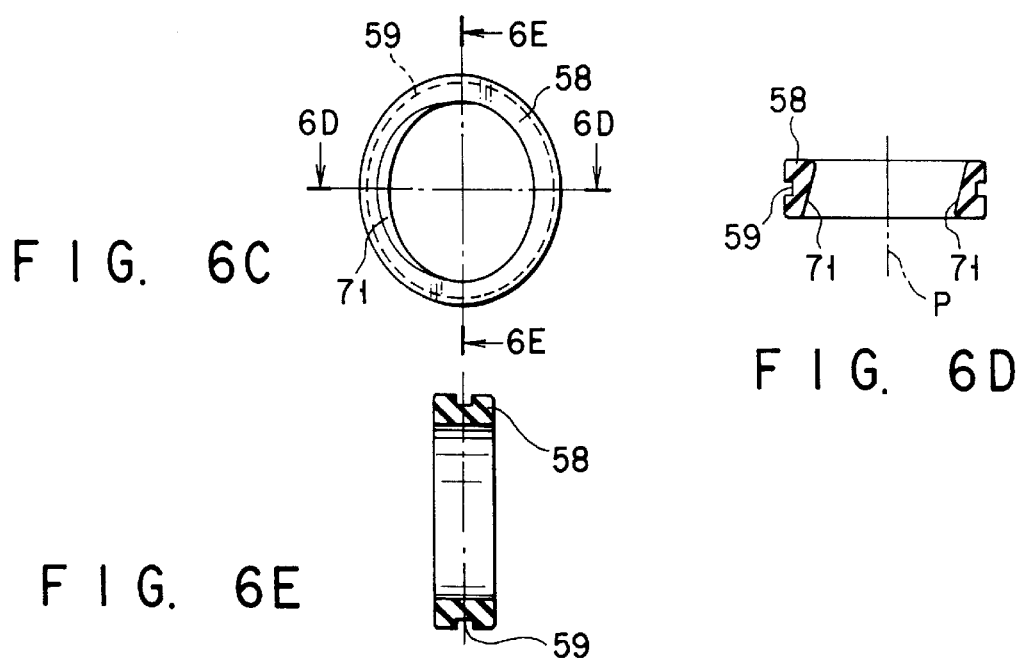
FIG. 6C
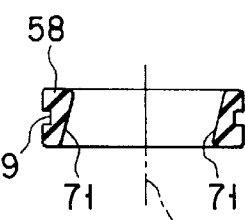
FIG. 6D
FIG. 6E

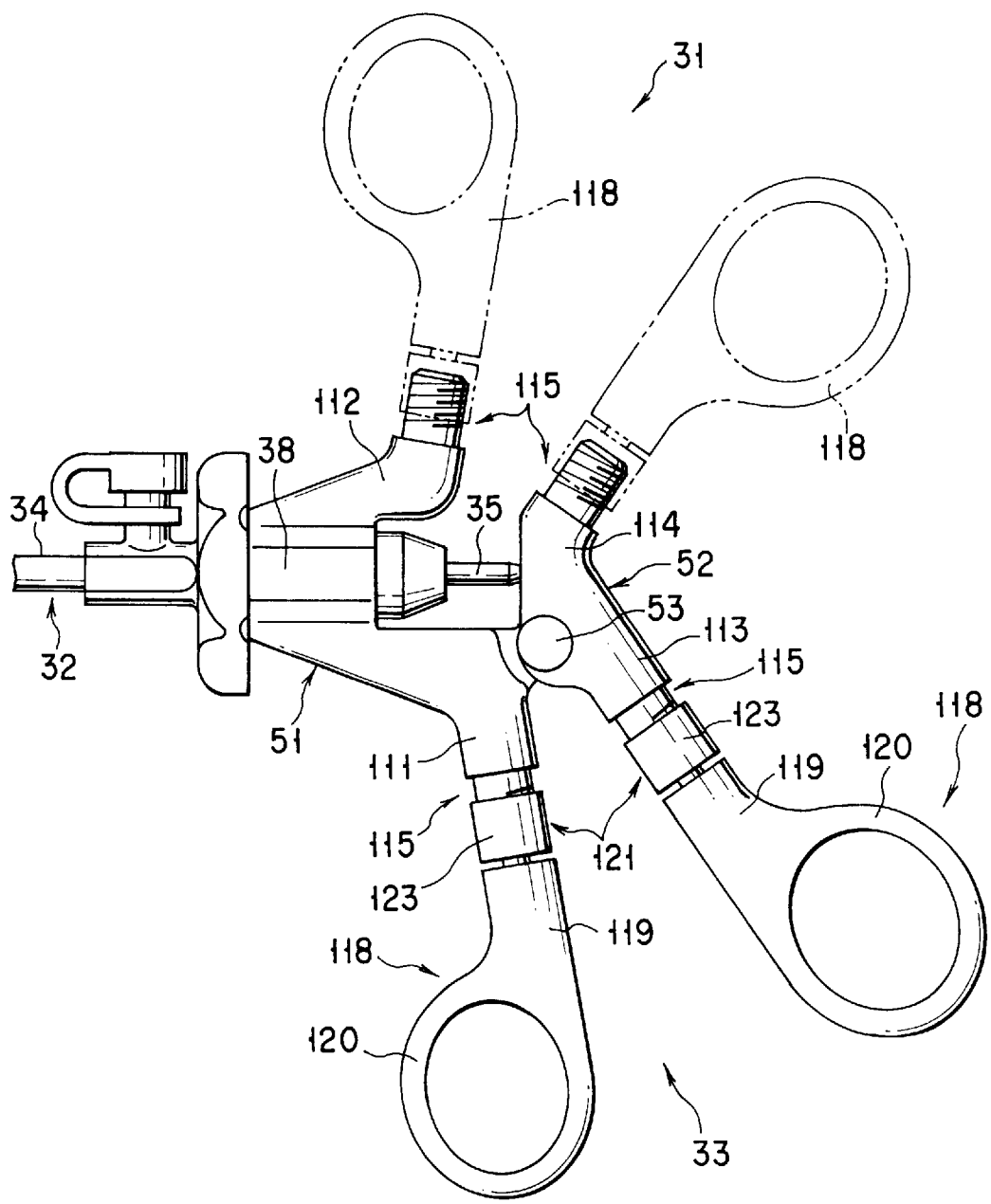
F I G. 10

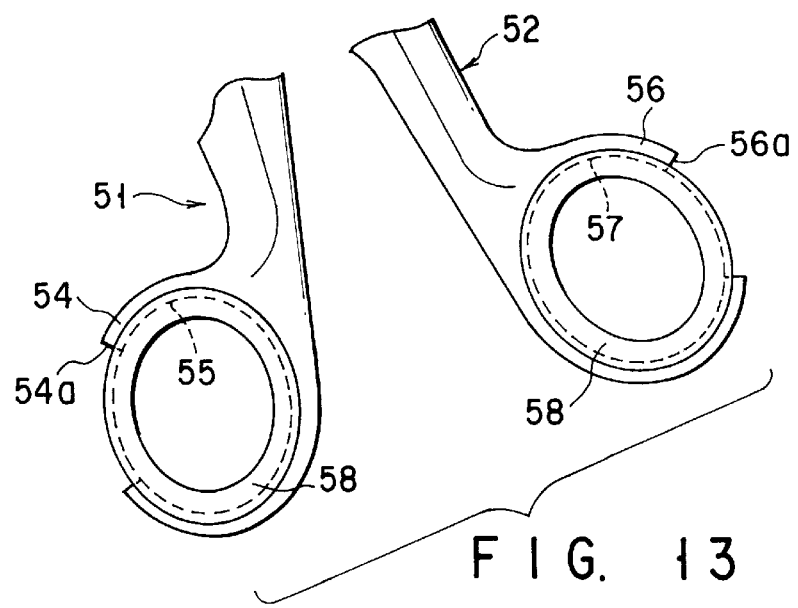
F I G. 13
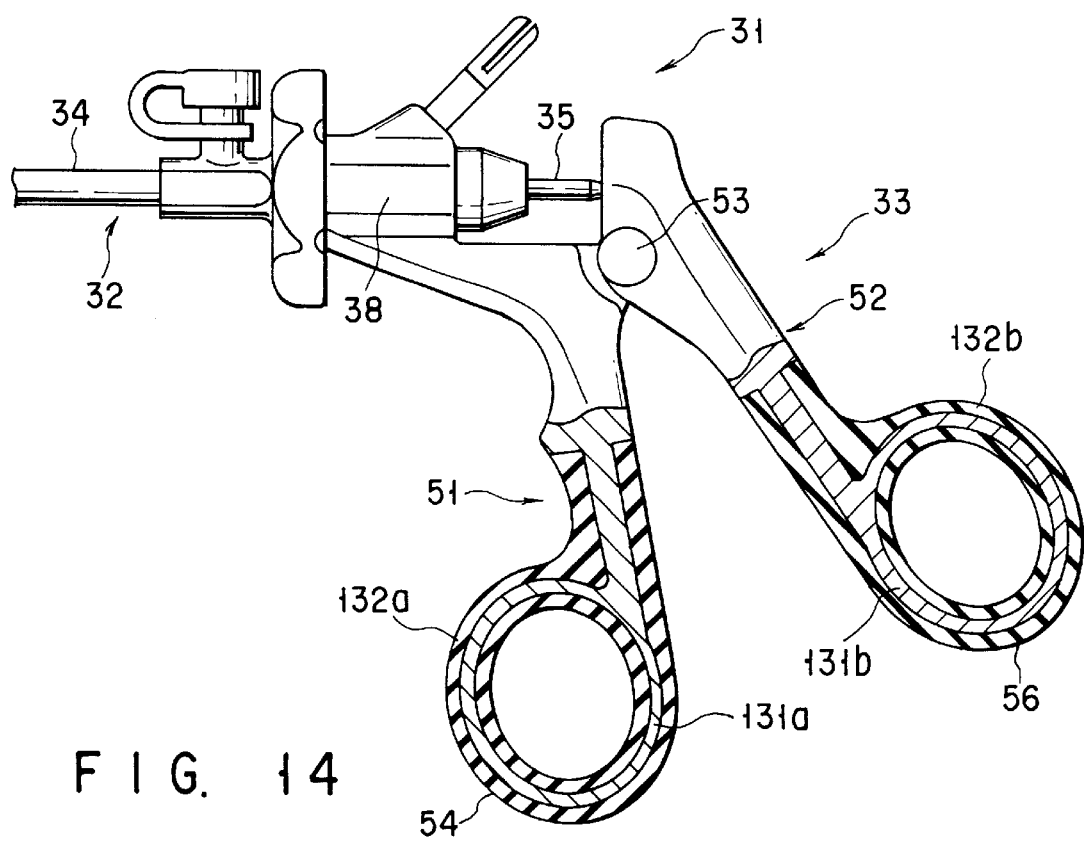
F I G. 14

TREATING INSTRUMENT FOR OPERATION AND MEDICAL DEVICE USING THE TREATMENT DEVICE

BACKGROUND OF THE INVENTION

The present invention relates to a treating instrument for an operation used in a surgical operation or an operation under an endoscope, and a medical device using the treating instrument.

Generally, as a treating instrument for an operation, there are surgical scissors as shown in Japanese Patent Application KOKOKU Publication No. 60-36293. As shown in FIG. 22A, this pair of scissors has two scissors pieces 1a and 1b. Two scissors pieces 1a and 1b are coupled to each other by a supporting pin 2 to be freely rotatable.

Moreover, this pair of scissors has an operation section 3, serving as handles, at a position closer to the base end portion side than the supporting pin 2. The operation section 3 has annular rings 4a and 4b for a finger insertion are inserted. Each of the rings 4a and 4b is formed on each of the base end portions of the scissors pieces 1a and 1b as one body. Then, an operator inserts his fingers 5 into the rings 4a and 4b of the operation section 3, and opens and closes a portion between two rings 4a and 4b. Thereby, cut edges 6a and 6b (treating section) of the top ends of the scissors pieces 1a and 1b are driven to be opened/closed.

Moreover, in Japanese Patent Application KOKAI Publication No. 4-246344, there is described a treating instrument used in the operation under the endoscope. This treating instrument has an insertion section, which is inserted to a human body, an operation section, which is provided on the side of the insertion section, and a treatment section, which is provided on the top end side of the insertion section. The operation section has a fixed handle and a movable handle, which is coupled to the fixed handle to be rotatable. Moreover, annular rings into which fingers are inserted are formed. Each of the rings is formed on each of the base end portion of each handle as one piece.

The treatment section has two openable/closable treatment members. Moreover, driving means is provided in the insertion section. Driving means transmits the operation of the movable handle of the operation section so to drive the treatment members. Then, the operator inserts his fingers 5 into two rings of the operation section, and opens and closes the movable handle of the operation section. Thereby, the treatment members of the treatment section on the top end portion are opened/closed by driving means.

In the conventional structure of the surgical scissors as shown in FIG. 22A, the rings 4a and 4b are arranged on a plane containing an axis X directing to a treating portion 8 from an operator's hand 7. Due to this, for moving the surgical scissors toward the treating portion 8 from an oblique direction, the operator must operate the surgical scissors in an unnatural state that the operator bends his wrist. As a result, there occurs a problem in which operator's fatigue and pain increase, thereby making it difficult to operate the treating instrument correctly. The same problem occurs in the treating instrument used in the operation under the endoscope of Japanese Patent Application KOKAI Publication No. 4-246344.

The rings 4a and 4b of the scissors pieces 1a and 1b are formed of metallic material or hard plastic material. Then, as shown in FIG. 22B, the cross-sectional shape of an inner peripheral surface 9 of each of rings 4a and 4b contacting the operator's finger 5 is substantially a plane. The width of each ring is narrow. As a result, there is a problem in which the end edge portion of the inner peripheral surface 9 of each ring acutely contacts the operator's finger 5. Due to this, if the operator operates the treating instrument such as the surgical scissors for a long period of time, there is the danger that the operator will have a pain in his fingers 5 inserted to the rings or have sensory trouble. Particularly, as compared with the scissors for stationery, the surgical scissors are often used for a long period time, and the operation of applying power to both opening and closing directions is frequently repeated. As a result, this kind of trouble frequently occurs. In this case, particularly, at the time of opening the treating instrument, low thickness portions such as a back portion of the finger and the hand, and the side portion, comes in contact with the rings 4a and 4b of the scissors pieces 1a and 1b. As a result, this contact exerts pressure on the nerves of operator's fingers and hand, and the operator easily feels a pain in his fingers and hand.

Moreover, the operator's fingers 5 inserted into the rings 4a and 4b are easily slid along the inner peripheral surface of the rings 4a and 4b, there is danger that the operator will erroneously operate the treating instrument such as surgical scissors.

BRIEF SUMMARY OF THE INVENTION

An object of the present invention is to provide a medical treating instrument which can be correctly operated with little operator's fatigue and pain, and provided a medical device using the treating instrument.

According to the present invention, there is provided a treating instrument for an operation comprising:

a main body of the treating instrument;

an operation section provided on a base end portion of the main body of treating instrument on an operator's side, the operation section having a first handle including first finger contacting means for contacting a part of an operator's finger, a second handle including second finger contacting means for contacting parts of the other operator's fingers, and coupling means for coupling the first and second handles to be relatively movable;

a treating section provided on the top end portion of the main body of the treating instrument, the treating section having a movable element, and the movable element operated in response to a relative moving operation between the first and second handles; and load reducing means for reducing a load of the operator's fingers contacting the first and second finger contacting means, and the load reducing means provided on a contact section contacting the operator's fingers of at least one of the first and second finger contacting means.

By use of the above-structured finger load reducing means, the load, which is applied on the operation fingers and wrist when operating the treating instrument, can be reduced. As a result, according to the present invention, there can be provided a treating instrument for an operation which can be correctly operated with little operator's fatigue and pain.

Moreover, according to the present invention, there is provided a medical device having a treating instrument for an operation and an endoscope combined, the treating instrument comprising:

a main body of the treating instrument;

an operation section provided on a base end portion of the main body of treating instrument on an operator's side, the operation section having a first handle including first finger contacting means for contacting a part of an operator's finger, a second handle including second finger contacting means for contacting parts of the other operator's fingers, and coupling means for coupling the first and second handles to be relatively movable;

a treating section provided on the top end portion of the main body of the treating instrument, the treating section having a movable element, and the movable element operated in response to a relative moving operation between the first and second handles; and load reducing means for reducing a load of the operator's fingers contacting the first and second finger contacting means, and the load reducing means provided on a contact section contacting the operator's fingers of at least one of the first and second finger contacting means; and the endoscope comprising observing means for observing an operation of the treating section.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1A is a side view showing a treating instrument for an operation of a first embodiment of the present invention;

FIG. 1B is a plane view showing the treating instrument for an operation of the first embodiment of the present invention;

FIG. 1C is a cross-sectional view cut along a line 1C—1C of FIG. 1A;

FIG. 2A is a side view showing a treating instrument for an operation of a second embodiment of the present invention;

FIG. 2B is a cross-sectional view cut along a line 2B—2B of FIG. 2A;

FIG. 3A is a side view of a treating instrument for an operation of a first modification of the second embodiment of the present invention;

FIG. 3B is a cross-sectional view cut along a line 3B—3B of FIG. 3A;

FIG. 4A is a plane view showing a first elastic ring provided on an operation section of the treating instrument of the first modification;

FIG. 4B is a plane view showing a second elastic ring of the first modification;

FIG. 4C is a plane view showing a third elastic ring of the first modification;

FIG. 4D is a cross-sectional view cut along a line 4D—4D of FIG. 4A;

FIG. 4E is a cross-sectional view cut along a line 4E—4E of FIG. 4B;

FIG. 4F is a cross-sectional view cut along a line 4F—4F of FIG. 4C;

FIG. 5A is a plane view of an elastic ring of a finger inserting section showing a second modification of the second embodiment;

FIG. 5B is a cross-sectional view cut along a line 5B—5B of FIG. 5A;

FIG. 6A is a plane view of an operation section showing a third modification of the second embodiment;

FIG. 6B is a cross-sectional view cut along a line 6B—6B of FIG. 6A;

FIG. 6C is a side view showing the elastic ring of the finger inserting section;

FIG. 6D is a cross-sectional view cut along a line 6D—6D of FIG. 6C;

FIG. 6E is a cross-sectional view cut along a line 6E—6E of FIG. 6C;

FIG. 10 is a plane view of an operation section showing a seventh modification of the second embodiment;

FIG. 13 is a side view of the operation section showing another modification of the first modification of the second embodiment;

FIG. 14 is a side view showing a partial cross-section of the operation section of an eighth embodiment of the second embodiment;

DETAILED DESCRIPTION OF THE INVENTION

Figures 7A, 7B:
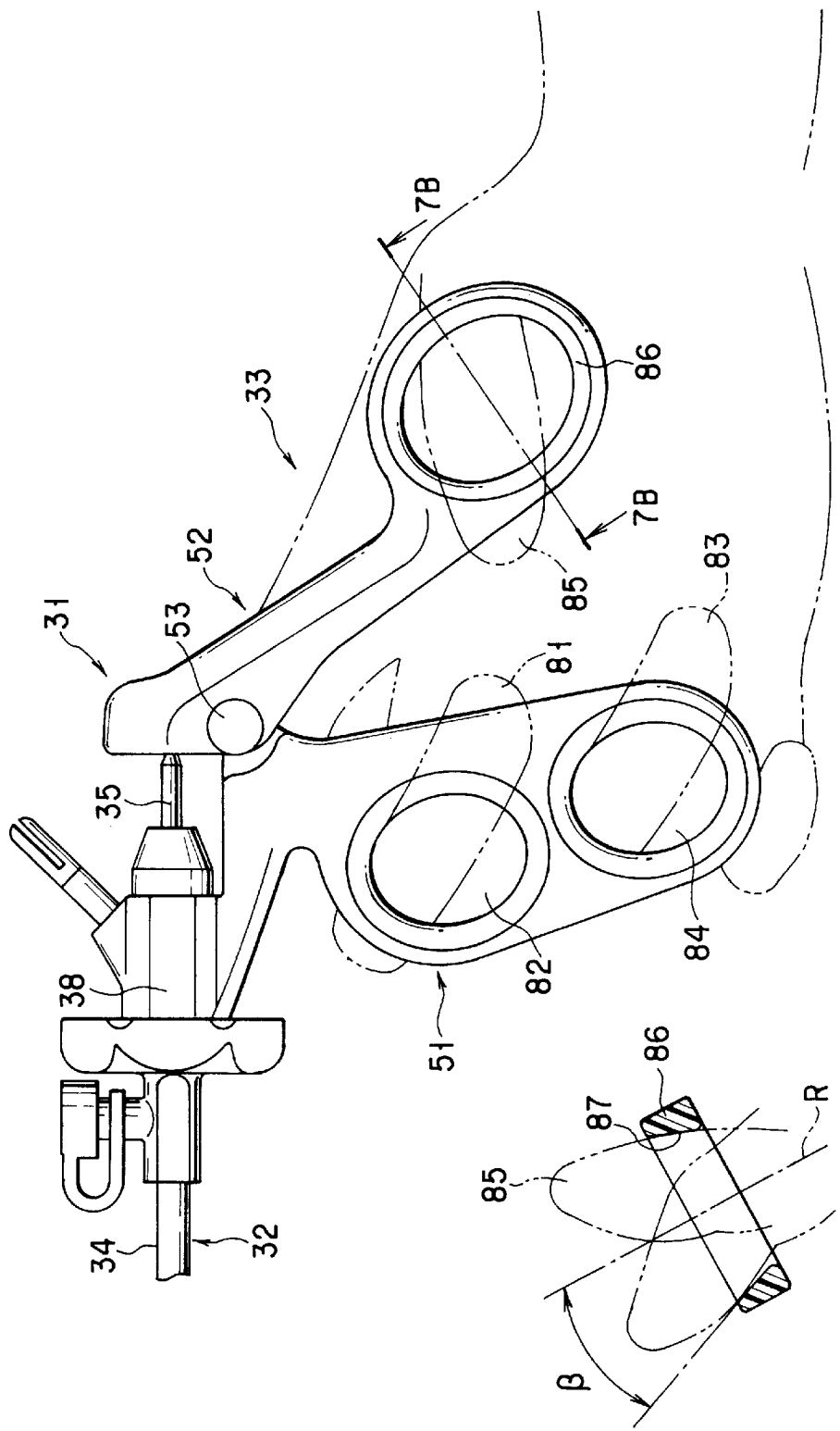
FIG. 7A is a plane view of an operation section showing a fourth modification of the second embodiment.
FIG. 7B is a cross-sectional view cut along a line 7B—7B of FIG. 7A.

The following will explain a first embodiment of the present invention with reference to FIGS. 1A to 1C.

FIGS. 1A and 1B show the schematic structure of a treating instrument 11 for an operation according to the present invention. The treating instrument has two (first and second) forceps 12a and 12b as shown in FIG. 1A. The forceps 12a and 12b are coupled to each other by a supporting pin (coupling means) 13 to be freely rotatable.

Also, the treating instrument 11 has an operation section 14, serving as handles, at a position closer to a base end portion side than the supporting pin 13, and a treatment section 15 at a position closer to a top end portion side than the support pin 13.

One first forceps 12a has a first handle element 16a provided in the operation section 14. An annular ring (first finger contacting means) 17a for a finger insertion is formed at an end portion of the first handle element 16a as one body. Also, the other second forceps 12b has a second handle element 16b provided in the operation section 14. An annular ring (second finger contacting means) 17b for a finger insertion is formed at an end portion of the second handle element 16b as one body.

Also, the treatment section 15 has extension sections (movable elements) 18a and 18b. The extension section 18a is formed to be extended to the top end portion of the first handle element 16a of the first forceps 12a as one body. The extension section 18b is formed to be extended to the top end portion of the second handle element 16b of the second forceps 12b as one body.

Moreover, in the treating instrument 11, on a contact portion where the rings 17a and 17b and the operator's fingers are contacted, there is provided finger load reducing means 11A for reducing the load on the operator's fingers contacting the rings 17a and 17b. The finger load reducing means 11A is structured as follows:

Specifically, the rings 17a and 17b are arranged on a plane Z inclined at a predetermined inclination angle α to an axis O connecting the operation section 14 to the treatment section 15 shown in FIG. 1A (axis O directing to a treating portion 20 from an operator's hand 19 using the treating instrument 11). The inclination angle α is set to a favorable range of 50 to 70°. Particularly, according to this embodiment, the inclination angle α is desirably set to substantially 60°.

The size of the ring 17a is so large that an operator's thumb 21 can be inserted. Also, the size of the ring 17b is so large that a single finger or a plurality of fingers 22 other than the thumb 21 can be inserted.

As shown in FIGS. 1B, and 1C, the second forceps 12b has a slit 23, which is formed at a coupling section between the forceps 12a and 12b. The first forceps 12a has a thin coupling portion, which is inserted to the slit 23 of the second forceps 12b.

Moreover, both end portions of the supporting pin 13 are fixed to wall portions 24a and 24b of the slit 23, respectively.

The coupling portion of the first forceps 12a is supported by the supporting pin 13 to be rotatable in a sliding state.

As shown in FIG. 1C, a coating layer 25, which is made of resin material having good sliding property such as PTFE, is formed on the inner surfaces of the peripheral wall portions 24a and 24b as one body. Moreover, a coating layer 26 is formed on a contact surface between the first forceps 12a and the wall portions 24a and 24b of the second forceps 12b, and a contact surface between the first forceps 12a and the supporting pin 13. The size of each of the coating layers 25 and 26 is set such that a gap between the first forceps 12a and the wall portion 24a and a gap between the first forceps 12a and the wall portion 24b are close to zero.

Next, the following will explain the function of the above-explained structure:

As shown in FIG. 1A, at the time of using the treating instrument 11, the operator's thumb 21 is inserted into the ring 17a of the first forceps 12a, and the single finger or the plurality of fingers 22 other than the thumb 21 is/are inserted into the ring 17b of the second forceps 12b. In this state, the opening and closing operation between the first handle element 16a of the first forceps 12a and the second handle element 16b of the second forceps 12b is performed. Thereby, the opening and closing between the extension sections 18a and 18b is driven. At this time, the contact surface between the forceps 12a and 12b and the contact surface between the first forceps 12a and the supporting pin 13 can be smoothly slid by the coating layers 25 and 26 without having gaps. As a result, the opening and closing between the first and second forceps 12a and 12b can be smoothly operated.

According to the above-structure, the following advantage can be brought about:

Specifically, the rings 17a and 17b are arranged on the plane Z inclined at the predetermined inclination angle α (substantially 60° in this embodiment) to an axis O connecting the operation section 14 to the treatment section 15 shown in FIG. 1A. In this case, axis O directs to the treating portion 20 from the operator's hand 19 using the treating instrument 11.

The operator's thumb 21 is inserted into the ring 17a of the first forceps 12a, and the single finger or the plurality of fingers 22 other than the thumb 21 is/are inserted into the ring 17b of the second forceps 12b. Under such an insertion state, if the operator opens and closes the operation section 14 in a natural state, the treating portion 20 is always positioned on the axis of an operator's forearm (not shown). As a result, even in a case where the treating instrument 11 is moved toward the treating portion 20 from the oblique direction, the operator can operate the treating instrument 11 in the natural state without bending his wrist. Therefore, the operator can correctly operate the treating instrument with a little fatigue and pain for a long period of time.

Moreover, in performing the opening/closing operation between the first handle element 16a of the first forceps 12a and the second handle element 16b of the second forceps 12b, the portion between the extension sections 18a and 18b of the treating section 15 can be smoothly operated by the coating layers 25 and 26 without having gaps.

FIGS. 2A and 2B show the second embodiment of the present invention in which the present invention is applied to a treating instrument for an operation 31 used under the operation using the endoscope.

The treating instrument 31 has an insertion section 32, which is inserted to a human body through a trocar sheath (not shown), and an operation section 33, which is coupled to the base portion of the insertion section 32.

The insertion section 32 also has a tubular insertion cylinder 34. Then, a drive shaft 35, which is relatively moved in an axial direction of the insertion section 32, is inserted to the tubular cylinder 34. A treatment section 36 is formed on the top end operation of the insertion section 32. The treatment section 36 has a pair of holding members (movable elements) 37, 37, which are openable and closable. The holding members 37, 37 are coupled to the top end of the driving shaft 35 through a driving mechanism (not shown), e.g., a cam mechanism. Then, a portion between the holding members 37, 37 of the treatment section 36 is opened/closed through the driving mechanism in accordance with the advancing and retreating operations of the driving shaft 35.

The operation section 33 has an operation main body 38 for holding the base end of the insertion section 32 to be freely rotatable. A fixed handle (first handle) 39 is formed on the operation main body 38 as one body. The fixed handle 39 has an arm 40 extending in substantially parallel to the axis of the insertion section 32.

Moreover, one end portion of a movable handle (second handle) 41, which is substantially L-shaped, is coupled to the fixed handle 39 through a supporting pin 42. The movable handle 41 has an arm-shaped handle body 43 and a short bending section 44. The arm-shaped handle body 43 extends in substantially parallel to the axis of the insertion section 32. The bending section 44 bends at substantially right angles from the one end portion of the handle body 43. Then, a free end of the bending section 44 is coupled to the fixed handle 39 through a supporting pin 42 to be freely rotatable. Moreover, an base end portion of the driving shaft 35 is coupled to the bending portion 44 of the movable handle 41.

A ring (first finger contacting means) 45 through which the operator's thumb can be inserted is coupled to the end portion of the arm 40 of the fixed handle 39 to be freely rotatable through a pin 46. A ring (second finger contacting means) 47 through which the operator's finger or fingers other than the thumb can be inserted is coupled to the end portion of the handle body 43 of the movable handle 41 to be freely rotatable through a pin 48.

Similar to the rings 17a and 17b of the first embodiment (FIGS. 1A to 1C), the rings 45 and 47 are arranged on a plane Z inclined at a predetermined inclination angle α to an axis O connecting the operation section 33 to the treatment section 36 (axis O directing to a treating portion 20 from an operator's hand using the treating instrument 31). The inclination angle α is set to a favorable range of 50 to 70°. Particularly, according to this embodiment, the inclination angle α is desirably set to substantially 60°.

Thus, hand and fingers load reducing means 31A for reducing load on operator's hand and fingers contacting both rings 45 and 47 is structured by the above-mentioned support structure of the ring 45 of fixed handle 39 and the ring 47 of the movable handle 41.

Next, the following will explain the function of the above-explained structure.

At the time of using the treating instrument 31, the operator's thumb is inserted into the ring 45 of the fixed handle 39a, and the single finger or the plurality of fingers other than the thumb is/are inserted into the ring 47 of the movable handle. In this state, the movable handle 41 is rotated to the fixed handle 39. At this time, the driving shaft 35 is axially moved to the insertion tube 34 of the insertion section 32 in accordance with the rotation of the movable handle 41. As a result, the portion between the holding members 37, 37 of the treatment section 36 can be opened and closed through the driving mechanism.

According to the above-structure, the following advantage can be brought about:

Specifically, the rings 45 and 47 are arranged on the plane Z inclined at the predetermined inclination angle α (substantially 60° in this embodiment) to an axis O connecting the operation section 33 to the treatment section 36. In this case, axis O directs to the treating portion from the operator's hand using the treating instrument 31.

The operator's thumb is inserted into the ring 45 of the fixed handle 39, and the single finger or the plurality of fingers other than the thumb is/are inserted into the ring 47 of the movable handle 41. Under such an insertion state, the operator can operate the treatment instrument 31 without bending his wrist in a natural state. As a result, similar to the first embodiment, the operator can correctly operate the treating instrument with a little fatigue and pain for a long period of time.

Moreover, in hand and fingers load reducing means 31A, the rings 45 and 47 are coupled to the arm 40 of the fixed handle 39 and the handle body 43 of the movable handle 41 through pins 46 and 48, respectively, to be freely rotatable. Thereby, the rings 45 and 47 can be rotated through pins 46 and 48 to follow in the movement of the operator'fingers inserted into the rings 45 and 47. As a result, there is an advantage in which the pain in the operator's fingers, which are inserted into the ring 45 and 47, respectively, can be reduced.

FIGS. 3A, 3B, FIGS. 4A to 4C, and FIGS. 4D to 4F show a first modification of the second embodiment (FIGS. 2A and 2B). In the first modification, the structure of the operation section 33 of the treating instrument for an operation 31 used under the operation using the endoscope is changed as follows: In this case, the same reference numerals are added to the same portions as the second embodiment.

More specifically, as shown in FIG. 3A, in the operation section 33 of the treating instrument 31 of the first modification, there is formed a fixed handle 51 together with the operation main body 38. The fixed handle 51 is bent in a substantially perpendicular to the axis of the insertion section 32. A movable handle 52 is coupled to the fixed handle 51 by a supporting member (coupling means) 53 to be freely movable. The base end portion of the drive shaft 35 is coupled to the head portion of the movable handle 52.

A ring-shaped finger inserting section 54 is formed at the end portion of the fixed handle 51. A projecting section 55 is projected over the entire inner peripheral surface of the finger inserting section 54 as shown in FIG. 3B.

Moreover, a ring-shaped finger inserting section 56 is formed at the end portion of the movable handle 52. A projecting section 57 is projected over the entire inner peripheral surface of the finger inserting section 56.

The inner peripheral surface of each of the finger inserting sections 54 and 56 is symmetrically shaped in its up and down, right and left, and back and forth portions. Moreover, the shape of the inner peripheral surface of the inserting section 54 is substantially the same as that of the finger inserting section 56.

An elastic ring (finger load reducing means) 58, which is formed of elastic material, is provided on each of the inner peripheral surfaces of the finger inserting sections 54 and 56 to be detachable as shown in FIG. 3B. On the outer peripheral surface of the elastic ring 58, there is formed an engaging groove 59, which can be engaged with each of the projecting sections 55 and 57.

The elastic ring 58 is formed of synthetic rubber of such as silicon rubber, fluororubber, butyl rubber, ethylene propylene rubber, isoprene rubber, butadiene rubber. The synthetic rubber is preferably anti-bacterial rubber. The width of the elastic ring 58 is preferably about 10 mm or more to increase a contact area with the fingers.

Next, the following will explain the function of the above-mentioned structure.

At the time of using the treating instrument 31, the operator's thumb is inserted into the elastic ring 58 of the finger inserting section 56, and the third finger (ring finger) or the second finger (the middle finger) is inserted into the elastic ring 58 of the finger inserting section 54. In this state, the movable handle 52 is rotated to the fixed handle 51. At this time, the driving shaft 35 is axially moved to the insertion tube 34 of the insertion section 32 in accordance with the rotation of the movable handle 52. As a result, the portion between the holding members 37, 37 of the treatment section 36 can be opened and closed through the driving mechanism.

Since the elastic ring 58 of each of the finger insertion sections 56 and 54 is formed of elastic material, and the elastic ring 58 is elastically deformed inwardly. Then, each of the projection sections 55 and 57 is engaged/disengaged with/from the engaging groove 59 of each elastic ring 58. Thereby, each elastic ring 58 can be easily attached/detached to/from each of the finger insertion sections 56 and 54.

Therefore, as shown in FIGS. 4A to 4C, and FIGS. 4D to 4F, a plurality of elastic rings 58A to 58C each having a different size of the inner peripheral surface (inner diameter) is prepared in advance. Thereby, the operator can select the elastic rings adjusting to operator's fingers.

There can be prepared several kinds of elastic rings 58 each having the same shape and a different hardness, e.g., range from JIS hardness of 30 to 80°. Moreover, the operator can easily discriminate the elastic rings 58A to 58C by adding marks e.g., S, M, L or changing a color in accordance with the size and the hardness of the elastic ring 58. Moreover, the elastic rings may be simply formed to be circular in place of an ellipse as shown in FIGS. 4A to 4C. In this case, the elastic rings 58 is attached to the finger inserting sections 54 and 56, so that the elastic ring 58 is deformed to the ellipse as shown in FIG. 3A.

According to the above-structure, the following advantage can be brought about:

Specifically, the elastic ring 58 of each of the finger inserting sections 56 and 54 is formed of elastic material. As a result, even in a long period of operation, the operator can operate the treating instrument with a little fatigue and pain in the operator's fingers inserted to the finger inserting sections 56 and 54.

Also, the operator can select the elastic rings 58 based on the use, the favorable size, shape, and hardness, and easily attach and detach the elastic rings to/from the finger inserting sections. Further, the elastic rings can be replaceable. As a result, the operability of the treating instrument and the wide use can be improved.

Moreover, if the elastic rings 58 are damaged, only the damaged elastic ring 58 may be replaced with new one, so that the initial operability can be easily recovered. Therefore, such elastic rings are excellent from the economical viewpoint.

FIGS. 5A and 5B show a second modification of the treating instrument 31 of the second embodiment (FIGS. 2A and 2B). In this second modification, the large number of minute projections 61 is formed on the inner peripheral surface of each of the elastic rings 58 of the first modification (FIGS. 3A, 3B, and FIGS. 4A to 4F).

In a case where the elastic ring 54 is attached to each of the finger inserting sections 56 and 54 of the first modification, the projections 61 formed on the inner peripheral portions of the elastic ring 58 serve as stoppers to prevent the operator's fingers from being slid on the inner peripheral surface of the elastic ring 58. In other words, by using the elastic ring 58 of this modification, the operator's fingers cannot be slid on the inner peripheral surface of the elastic ring 58, so that the erroneous operation of the treating instrument 31 can be prevented.

Moreover, in a case where the projections 61 on the inner peripheral surface of the elastic ring 58 are worn down, only the elastic ring 58 is replaced with new one, so that the initial operability can be easily recovered.

FIGS. 6A to 6E show a third modification of the treating instrument 31 of the second embodiment (FIGS. 2A and 2B). Inclination surfaces 71, which are inclined to an axis P of the elastic ring 58, are formed at right and left portions (in FIG. 6C) on the inner peripheral surface of the elastic ring 58 of the treating instrument 31 of the first modification (FIGS. 3A, 3B, and FIGS. 4A to 4F) to be substantially parallel to each other a shown in FIG. 6D. In this case, the inner peripheral shape of the elastic ring 58 may be the same as that of the ring of ring-shaped finger inserting section 155 and 156 of a tenth modification (FIG. 16 and FIGS. 17A to 17D) to be described later.

According to the above-mentioned structure, as shown in FIGS. 6A and 6B, the elastic rings 58 are mounted on the finger inserting section 56 of the movable handle 52 and the finger inserting section 54 of the fixed handle 51. At this time, operator's fingers 72 and 73 inserted into the elastic rings 58 come in contact with an inclination surfaces 71 of the inner peripheral surfaces of the elastic rings 58 in substantially parallel. As a result, at the time of operating the treating instrument 31, pressure applied to the operator's fingers 72 and 73 is reduced. Due to this, there is an advantage in which the load on the operator's fingers 72 and 73 is decreased.

FIGS. 6A and 6B showed the elastic rings 58, which are formed to be suitable for the operator's right. However, elastic rings 58 are rotated at 180° around the axis Q from the state of FIGS. 6A and 6B, and mounted on the finger inserting section 56 of the movable handle 52 of the first modification (FIGS. 3A and 3B) and the finger inserting section 54 of the fixed handle 51. Thereby, the elastic rings 58 can be changed to have the shapes, which are suitable for the operator's left hand.

FIGS. 7A and 7B show a fourth modification of the treating instrument 31 of the second embodiment (FIGS. 2A and 2B). In this modification, the structure of the operation section 33 of the first modification (FIGS. 3A and 3B) is changed as follows. In this case, the structure of the parts other than the operation section 33 are the same as the treating instrument 31 of the second embodiment. The same reference numerals are added to the portions common to the second embodiment, and the explanation is omitted.

Specifically, as shown in FIG. 7A, in the operation section 33 of the treating instrument 31 of this modification, the fixed handle 51 has a substantially elliptic finger insertion hole 82 through which operator's middle finger (second finger) 81 is inserted and a finger insertion hole 84 through which a substantially elliptic operator's ring finger (third finger) is inserted.

Also, at the end of the movable handle 52, a substantially elliptic ring 86 through which an operator's thumb 85 is inserted is formed as one body. An inclination surface 87, which is inclined to an axis R, is formed on the entire inner peripheral surface of the ring 86 as shown in FIG. 7B.

In this modification, an inclination angle β of the inclination surface 87 to the axis R of the ring 86 of the movable handle 52 is set to about 20°. Moreover, the inclination surface 87 is also formed on the entire inner peripheral surfaces of the finger inserting holes 82 and 84.

At the time of using the treating instrument 31, the operator's thumb 85 is inserted into the ring 86 of the movable handle 52, the middle finger 81 is inserted into the hole 82 of the fixed handle 51, and the ring finger 83 is inserted to the hole 84. In this state, the movable handle 52 is rotated to the fixed handle 51. At this time, the driving shaft 35 is axially moved to the insertion tube 34 of the insertion section 32 in accordance with the rotation of the movable handle 52. As a result, the portion between the holding members 37, 37 of the treatment section 36 can be opened and closed through the driving mechanism.

As mentioned above, the inclination surface 87, which is inclined to the axis R, is formed on the entire inner peripheral surface of the ring 86 of the movable handle 52. As a result, the operator's thumb 85 inserted into the ring 86 of the movable handle 52 comes in contact with the inclination surface 87 substantially in parallel. Due to this, at the time of operating the treating instrument 31, pressure applied to the operator's thumb 85 is reduced. Due to this, there is an advantage in which the load on the operator's thumb 85 is decreased.

Moreover, similar to the ring 86 of the movable handle 52, the inclination surface 87 is formed on the entire inner peripheral surfaces of the finger inserting holes 82 and 84. As a result, similar to the operator's thumb 85, the load on the operator's load on the middle finger 81 and the ring finger 83 can be reduced at the time of operating the treating instrument 31. In other words, since the load on the respective fingers operating the treating instrument 31 can be reduced, the operator's fatigue and pain can be decreased.

Figure 8:
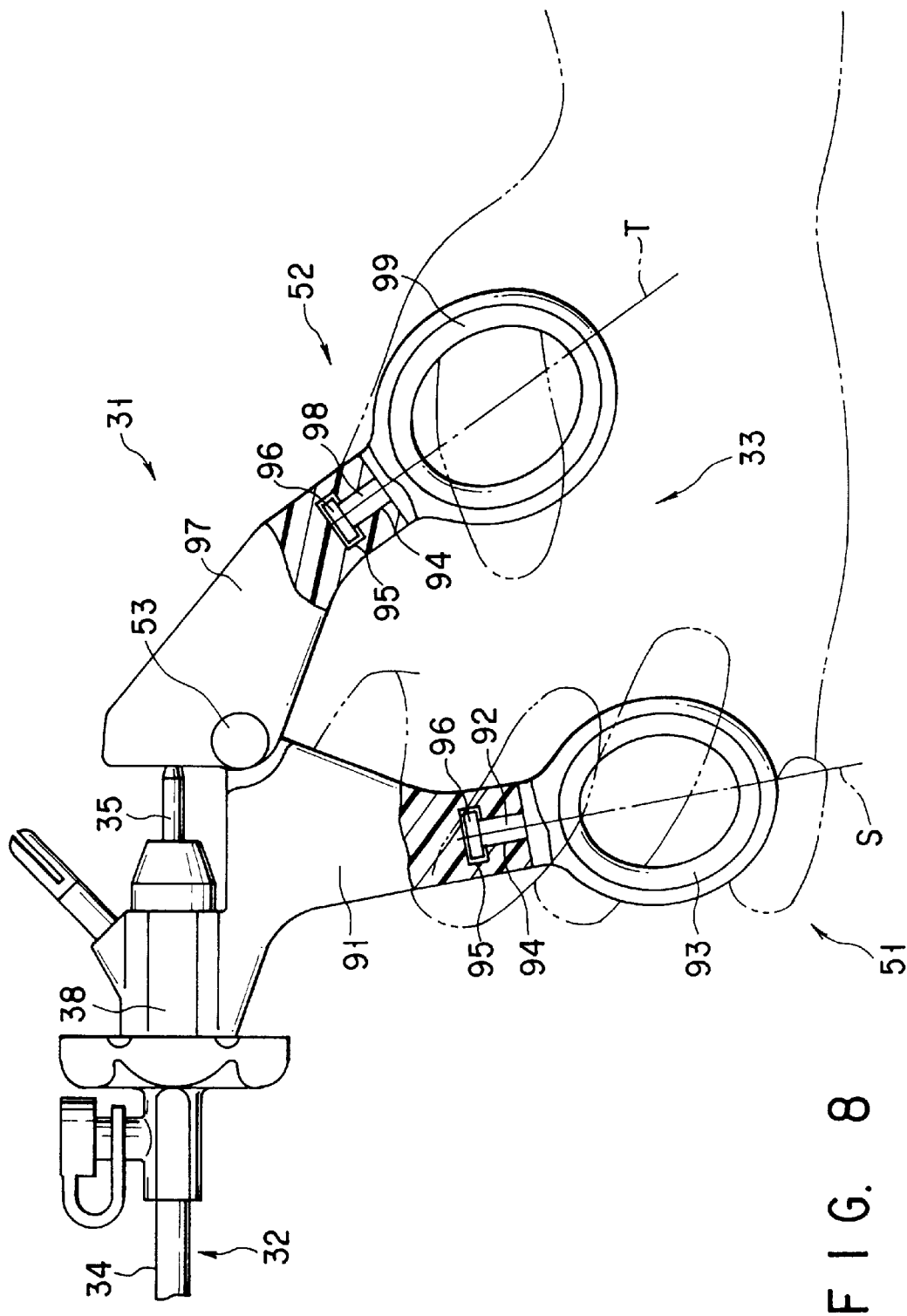
FIG. 8 is a plane view of an operation section showing a fifth modification of the second embodiment.

FIG. 8 shows a fifth modification of the treating instrument 31 of the second embodiment (FIGS. 2A and 2B). In this modification, the structure of the operation section 33 of the first modification (FIGS. 3A and 3B) is changed as follows. In this case, the structure of the parts other than the operation section 33 are the same as the treating instrument 31 of the second embodiment. The same reference numerals are added to the portions common to the second embodiment, and the explanation is omitted.

More specifically, as shown in FIG. 8, the treating instrument 31 of this modification has a handle main body 91 and a ring-shaped member 93 for a finger insertion. The handle main body 91 is formed on the fixed handle 51 of the operation section 33 together with the operation section 38 as one body. The ring-shaped member 93 is coupled to the end portion of the handle main body 91 to be freely rotatable around a rotation shaft 92.

An engaging groove 94 is formed on the end portion of the handle main body 91 of the fixed handle 51. The engaging groove 94 has a large-diameter hole 95 on its inner end portion (upper end portion in FIG. 8).

On the ring-shaped member 93, the rotation shaft 92, which engages with the engaging groove 94 of the handle main body 91, is formed to be projected. A thick diameter section 96, which is inserted into the large-diameter hole 95, is formed at the top end portion of the shaft 92. The ring-shaped member 93 is coupled to the end portion of the handle main body 91 to be freely rotatable around a rotation shaft 92.

Similarly, a handle main body 97 is formed on the movable handle 52. Also, a ring-shaped member 99 for a finger insertion is coupled to the end portion of the handle main body 97 to be freely rotatable around a rotation shaft 98. The coupling mechanism of the free rotation between the handle main body 97 of the movable handle 52 and the ring-shaped member 99 has the same structure as the fixed handle 51. Then, the same reference numerals are added to the same portions, and the explanation is omitted.

The inclination surface, which is similar to the ring 86 of the fourth modification (FIGS. 7A and 7B), is formed on the entire inner peripheral surface of each of the ring-shaped member 93 of the fixed handle 51 and the ring-shaped member 99 of the movable handle 52.

At the time of using the treating instrument 31, the operator's thumb is inserted into the ring-shaped member 99 of the movable handle 52, the middle finger or the ring finger is inserted into the ring-shaped member 93 of the fixed handle 51.

In this state, the movable handle 52 is rotated to the fixed handle 51. At this time, the driving shaft 35 is axially moved to the insertion tube 34 of the insertion section 32 in accordance with the rotation of the movable handle 52. As a result, the portion between the holding members 37, 37 of the treatment section 36 can be opened and closed through the driving mechanism.

Moreover, in the treating instrument 31 of this modification, at the rotation time of the movable handle 52, the ring-shaped member 99 follows the operator's thumb inserted into the ring-shaped member 99, and rotates around the rotation shaft 98 to the handle main body 97. Also, the ring-shaped member 93 follows the middle or ring finger inserted into the ring-shaped member, and rotates around the rotation shaft 92 to the handle main body 91. At this time, since the large-diameter portion 96 is formed at the top end of the rotation shafts 92 and 98, the ring-shaped members 93 and 99 are not moved in the axial direction of the rotation shafts 92 and 98.

According to the above-explained structure, at the operation time of the treating instrument 31, the ring-shaped members 93 and 99 follow the respective fingers and rotate. As a result, the pain in the operator's fingers can be further reduced.

In the fifth embodiment of FIG. 8, the ring-shaped members 93 and 99 are formed to be suitable for the operator's right hand. However, the ring-shaped members 93 and 99 are rotated at 180° around the axes S and T from the state of FIG. 8, respectively. Thereby, the ring-shaped members 93 and 99 can be changed to have the shapes, which are suitable for the operator's left hand. As a result, there can be obtained the shape of the operation section 33, which is suitable for the operation with both right and left hands.

Figure 9:
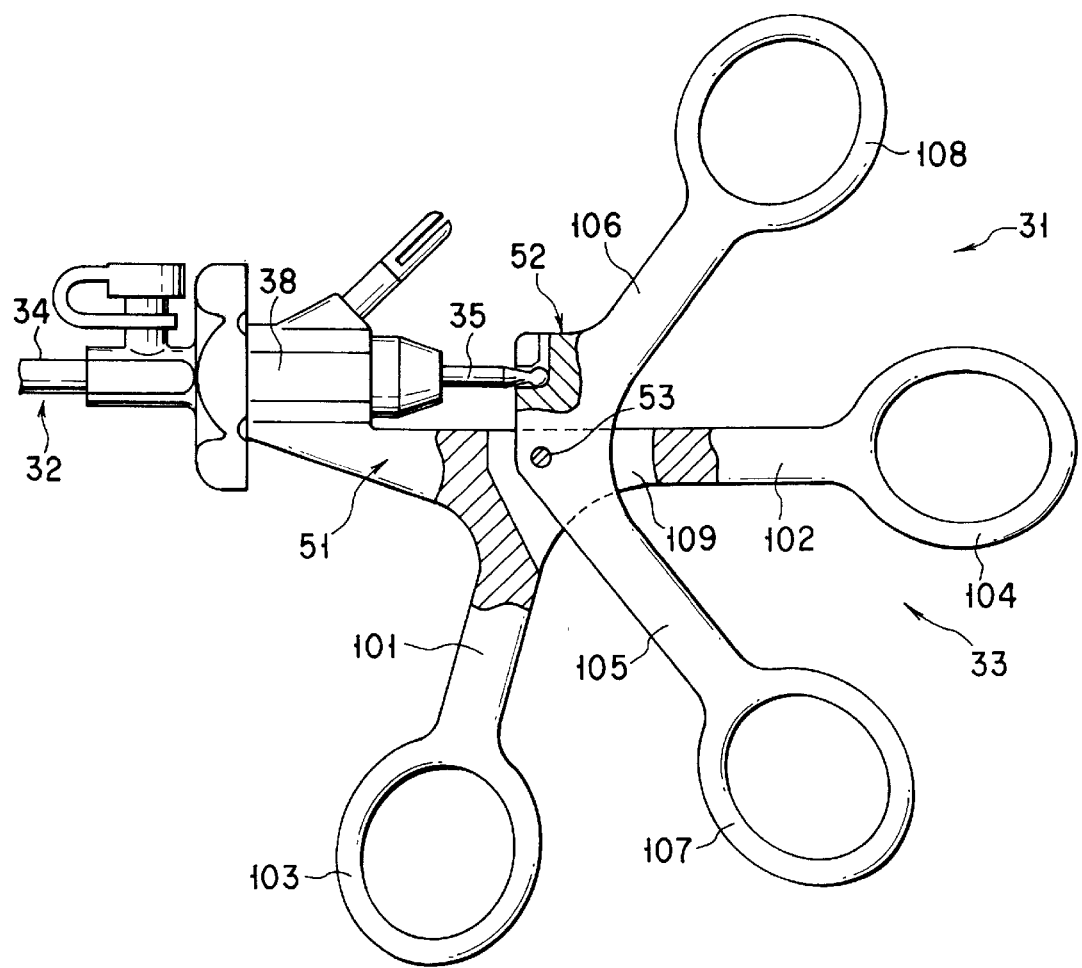
FIG. 9 is a plane view of an operation section showing a sixth modification of the second embodiment.

FIG. 9 shows a sixth modification of the treating instrument 31 of the second embodiment (FIGS. 2A and 2B). In this modification, the structure of the operation section 33 of the first modification (FIGS. 3A and 3B) is changed as follows. In this case, the structure of the parts other than the operation section 33 are the same as the treating instrument 31 of the second embodiment. The same reference numerals are added to the portions common to the second embodiment, and the explanation is omitted.

More specifically, in the treating instrument 31 of this modification, as shown in FIG. 9, the fixed handle 51, which is formed with the operation section 38 as one body, has two arms 101 and 102 (lower first arm 101 and upper second arm 102). The arms 101 and 102 are expanded to be substantially V-shaped. An opening angle between two arms 101 and 102 is set to about 110°. Moreover, annular rings 103 and 104 are formed on the end portions of the arms 101 and 102 as one body, respectively.

Moreover, the movable handle 52, which is coupled to the fixed handle 51 to be freely rotatable by the supporting member 53, has two arms 105 and 106 (lower third arm 105 and upper fourth arm 106). The arms 105 and 106 are expanded to be substantially V-shaped. An opening angle between two arms 105 and 106 is set to about 110°. Moreover, annular rings 107 and 108 are formed on the end portions of the arms 105 and 106 as one body, respectively.

The fixed handle 51 has a slit 109 for inserting movable handle 52, which is formed at a coupling portion between the arms 101 and 102. One arm (third arm) 105 of the movable handle 52 is extended between two arms 101 and 102 of the fixed handle 51 through the slit 109, and the movable handle 52 is coupled to the fixed handle 51 to be freely rotatable by the supporting member 53. In this case, the third arm 105 is placed at an intermediate position between the arms 101 and 102. In other words, the movable handle 52 is positioned such that the angle between the first and third arms 101 and 105, the angle between the third and second arms 105 and 102, and the angle between the second arm and the fourth arm 102 and 106 are equal to each other.

The slit 109 into which the third arm 105 is inserted has a space large enough to insert a cleaning blush (not shown).

Then, at the time of using the treating instrument 31 of this modification, the operator can selectively use the rings 103 and 104 of the arms 101 and 102 and the rings 107 and 108 of the arms 105 and 106 by depending on the situation of using the treating instrument 31. In other words, there are three combinations, that is, a first combination in which the ring 103 of the first arm 101 and the ring 107 of the third arm 105 are used, a second combination in which the ring 107 of the third arm 105 and the ring 104 of the second arm 102 are used, and a third combination in which the ring 104 of the second arm 102 and the ring 108 of the fourth arm 106 are used. Then, any one of these combinations can be selected by depending on the situation.

The movable handle 52 is rotated around the supporting member 53 to the fixed handle 51 by any one of these combinations. At this time, the driving shaft 35 is axially moved to the insertion tube 34 of the insertion section 32 in accordance with the rotation of the movable handle 52. As a result, the portion between the holding members 37, 37 of the treatment section 36 can be opened and closed through the driving mechanism.

At the time of the opening and closing operation of the operator's hand, the closing operation can generally generate larger force than the opening operation. Therefore, when the operator operates the treating instrument 31 by the first and third combinations, a large amount of force is generated in a direction where the driving shaft 35 is retreated.

Conversely, when the operator operates the treating instrument 31 by the second combination, a large amount of force is generated in a direction where the driving shaft 35 is advanced.

According to the above-explained structure, the operator can selectively use the rings 103 and 104 of the arms 101 and 102 and the rings 107 and 108 of the arms 105 and 106 by depending on the situation of using the treating instrument 31 (e.g., angle to the insertion section 32, amount of force, etc). As a result, there can be obtained an advantage in which operability of the treating instrument 31 is improved.

In a case where the treating instrument 31, which is operated by the first combination during the operation, is handed to the other operator (e.g., assistance), the other operator inserts his fingers into the rings 104 and 108. Thereby, the treating instrument 31 can be handed to the other operator without stopping the operation of the treating instrument 31. As a result, the operation time can be shortened.

Moreover, the above-mentioned treating instrument is the simple structure, and the slit 109 into which the third arm 105 is inserted has a space large enough to insert a cleaning blush (not shown). As a result, there can be obtained an advantage in which cleanness is improved.

Figure 11:
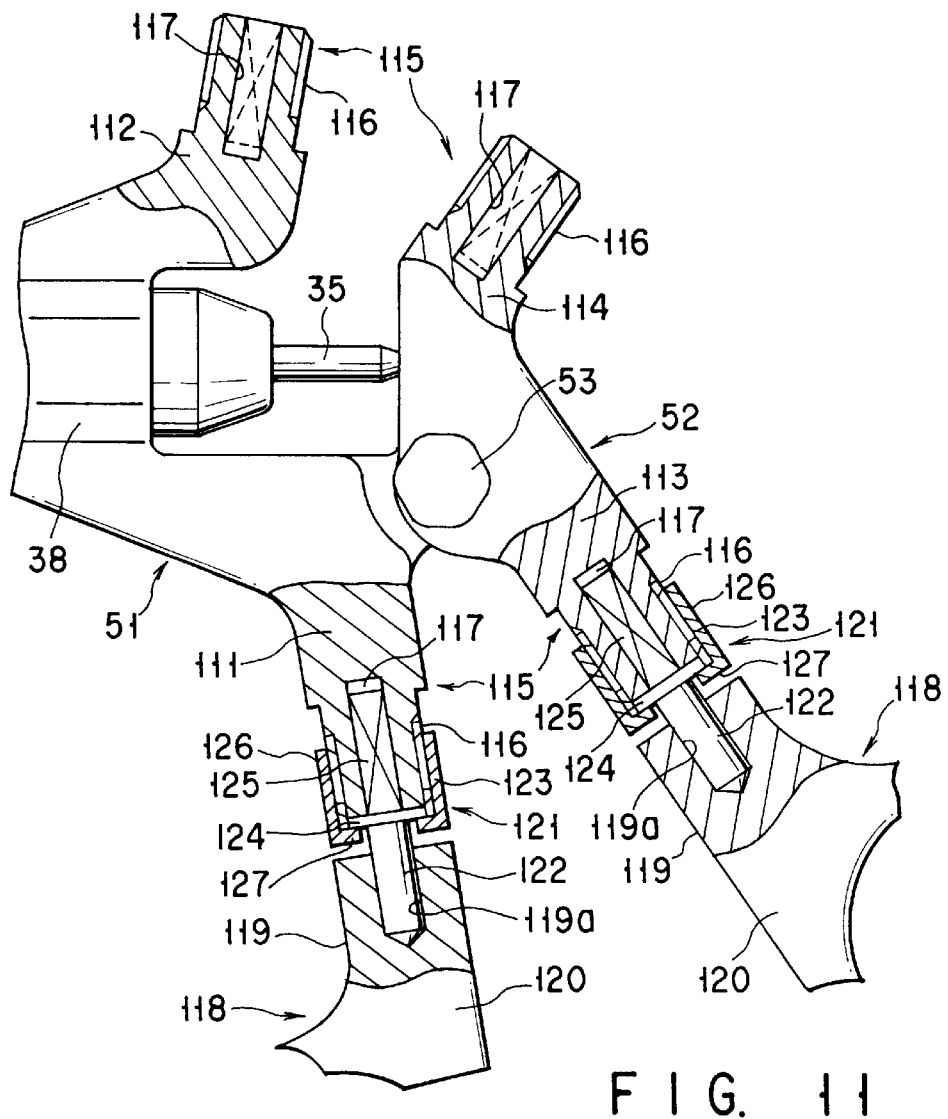
FIG. 11 is a side view showing a partial cross-section of the operation section of the seventh modification.
Figure 12:
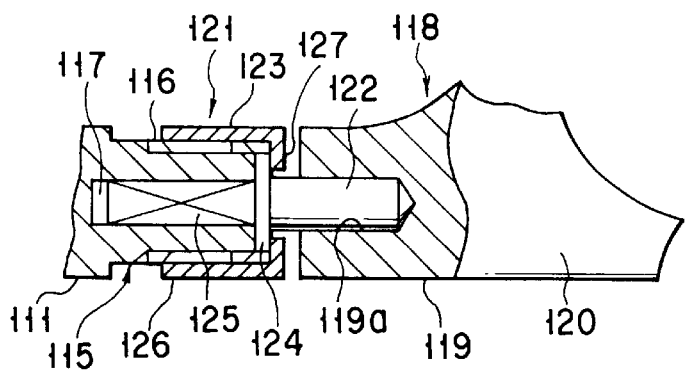
FIG. 12 is a side view showing a partial cross-section of a coupling section between a switchable ring and a handle body of the operation section of the seventh modification.

FIGS. 10 to 12 show a seventh modification of the treating instrument 31 of the second embodiment (FIGS. 2A and 2B). In this modification, the structure of the operation section 33 of the first modification (FIGS. 3A and 3B) is changed as follows. In this case, the structure of the parts other than the operation section 33 are the same as the treating instrument 31 of the second embodiment. The same reference numerals are added to the portions common to the second embodiment, and the explanation is omitted.

More specifically, in the treating instrument 31 of this modification, as shown in FIG. 10, the fixed handle 51, which is formed with the operation section 38 as one body, has a first arm 111 and a second arm 112. The first arm 111 extends to the lower side of the operation section 38, and the second arm 112 extends to the upper side of the operation section 38.

Moreover, the movable handle 52, which is coupled to the fixed handle 51 to be freely rotatable by the supporting member 53, has a third arm 113 and a fourth arm 114. The third arm 113 extends to the lower side of the supporting member 53, and the fourth arm 114 extends to the upper side of the supporting member 53.

A connecting section 115 is formed on the t op end portion of each of the first to fourth arms 111 to 114. The shapes of the connecting sections 115 of these arms are all the same. As shown in FIGS. 11 and 12, each of these connecting sections 115 has a male screw 116 and a hole 117, which is formed at the center of the male screw 116. A plane for positioning is formed on one side surface of the inner peripheral surface of each of the hole 117.

A ring-shaped material 118 is connected to the connecting section 115 of the first arm 111 of the fixed handle 51 to be detachable. The ring-shaped material 118 has a coupling arm 119 and a ring 120 for finger insertion, which is formed at the base end portion of the coupling arm 119 as one body.

Moreover, a coupling member 121 is fixed to the top end portion of the coupling arm 119 as one body. The coupling member 121 has a rod-shaped member 122 and a female member 123.

The base end portion of the rod-shaped member 122 is inserted to a hole 119a formed at the top end portion of the coupling arm 119 as one body. Moreover, the top end portion of the rod-shaped member 122 is projected to the outside of the hole 119a. The projecting portion of the rod-shaped member 122 has a thick portion 124 for preventing the female screw 123 from being detached and an engage projection section 125, which is inserted into the hole 117 of the connecting section 115.

Moreover, the female screw 123 has a female screw 126, which is fit to the male screw 116 of the connecting section 115, and a ring-shaped thin diameter portion 127 whose diameter is smaller than the thick portion 124 of the rod-shaped member 122. The female screw 123 is held to be freely rotatable along the rod-shaped member 122 and to be freely movable in an axial direction of the rod-shaped member 122. The moving range of the rod-shaped member 122 of the female screw 123 to the axial direction is restricted by the thick diameter section 124 of the rod-shaped member 122.

Similar to the connecting section 115 of the first arm 111 of the fixed handle 51, the ring-shaped member 118 is coupled to the connecting section 115 of the third arm 113 of the movable handle 52 to be freely detachable. The structure of the ring-shaped member 118 coupled to the third arm 113 is the same as the ring-shaped member 118 coupled to the first arm 115, and the explanation is omitted.

Each of the ring-shaped members 118 detached from each of the connecting sections 115 of the first and third arms 111 and 113 is coupled to each of the connecting sections 115 of the second and fourth arms 112 and 114, as required.

Then, the treating instrument 31 can be used in a first state or a second state as explained below:

Specifically, in the first state, as shown in FIGS. 10 and 11, the ring-shaped member 118 is coupled to each of the connecting sections 115 of the first and third arms 111 and 113 to be freely detachable. In the second state, each of the ring-shaped members 118 detached from each of the connecting sections 115 of the first and third arms 111 and 113 is coupled to each of the connecting sections 115 of the second and fourth arms 112 and 114, to be freely detachable as shown by an imaginary line of FIG. 10.

The engage projection section 125 of the ring-shaped member 118 is inserted to the hole 117 of each of the connecting sections 115 of each of the first and third arms 113. In such a state, the female screw 123 of the ring-shaped member 118 is rotated in a screw direction to the male screw 116 of each connecting section 115. Thereby, as in the first state shown in FIGS. 10 and 11, the ring-shaped member 118 is coupled to each of the connecting sections 115 of the first and third arms 111 and 113 to be freely detachable.

Under this state, the operator performs the closing operation of the ring-shaped member 118 of the third arm 113 of the movable handle 52 with his fingers to rotate the movable handle 52 to the fixed handle 51 around the supporting member 53 clockwise in FIGS. 10 and 11. Thereby, the drive shaft 35 is retreated in the axial direction to the insertion tube member 34 of the insertion section 32 in accordance with the rotation of the movable handle 52. In other words, a large amount of force can be generated in a direction where the drive shaft 35 is retreated. At this time, the portion between the holding members 37, 37 of the treatment section 36 can be opened and closed through the driving mechanism.

The female screw 123 of the ring-shaped member 118 is rotated in a direction opposite to the screwing direction from the male screw 116 of each connecting section 115 of each of the first arm 111 of the fixed handle 51 and the third arm 113 of the movable handle 52 in the first state shown in FIGS. 10 and 11. Then, the engage projection portion 125 is pulled out from the hole 117 of the connecting section 115. Thereby, the ring-shaped member 118 can be detached from each connecting section 115 of each of the first arm 111 of the fixed handle 51 and the third arm 113 of the movable handle 52.

Moreover, the engage projection portion 125 of the detached ring-shaped member 118 is inserted into the hole 117 of each of the connecting section 115 of each of the second arm 112 and the fourth arm 114. In such a state, the female screw 123 of the ring-shaped member 118 is rotated in a screw direction to the male screw 116 of each connecting section 115. Thereby, as in the second state shown by the imaginary line of FIG. 10, the ring-shaped member 118 is coupled to each of the connecting sections 115 of the second and fourth arms 112 and 114 to be freely detachable.

Under this state, the operator performs the closing operation of the ring-shaped member 118 of the fourth arm 114 of the movable handle 52 with his fingers to rotate the movable handle 52 to the fixed handle 51 around the supporting member 53 anticlockwise in FIGS. 10 and 11. Thereby, the drive shaft 35 is advanced in the axial direction to the insertion tube member 34 of the insertion section 32 in accordance with the rotation of the movable handle 52. In other words, a large amount of force can be generated in a direction where the drive shaft 35 is advanced. At this time, the portion between the holding members 37, 37 of the treatment section 36 can be opened and closed through the driving mechanism.

According to the above-explained structure, the first arm 111, which extends to the lower side of the operation section 38, and the second arm 112, which extends to the upper side of the operation section 38, are provided on the fixed handle 51. Moreover, the third arm 113, which extends to the lower side of the supporting member 53, and the fourth arm 114, which extends to the upper side of the supporting member 53 are provided on the movable handle 52. Then, since the treating instrument 31 can be used in the first state or the second state, the operation section 33 can be used by depending on the using situation. That is, in the first state, as shown in FIGS. 10 and 11, the ring-shaped member 118 is coupled to each of the connecting sections 115 of the first and third arms 111 and 113 to be freely detachable. In the second state, each of the ring-shaped members 118 detached from each of the connecting sections 115 of the first and third arms 111 and 113 is coupled to each of the connecting sections 115 of the second and fourth arms 112 and 114, to be freely detachable as shown by an imaginary line of FIG. 10. As a result, there can be obtained an advantage in which operability of the treating instrument 31 is improved.

Next, FIG. 13 shows another modification of the first modification (FIGS. 3A and 3B). In this modification, the structure of the operation section 33 of the first modification is changed as follows. In this case, the structure of the parts other than the operation section 33 are the same as the treating instrument 31 of the second embodiment. The same reference numerals are added to the portions common to the second embodiment, and the explanation is omitted.

More specifically, in this modification, each of notches 54a and 56a are provided on each of the finger inserting sections 54 and 56. Each of notches 54a and 56a is formed by cutting a part of the circumference of the ring. Then, the elastic ring 58 is inserted into the ring of each of substantially C-shaped finger inserting sections 54 and 56.

As explained above, the notches 54a and 56a are formed on the finger insertion sections 54 and 56 by cutting the part of the circumference of the inserting sections 54 and 56. Due to this, in operating the operation section 33 in an opening direction, the elastic ring 58 can be largely deformed at the portions of the notches 54a and 56a. As a result, it is possible to further effectively reduce the pain in the fingers caused when the operation section 33 is operated in the opening direction.

FIG. 14 shows an eighth modification of the treating instrument 31 of the second embodiment (FIGS. 2A and 2B). In this modification, the structure of the operation section 33 of the first modification (FIGS. 3A and 3B) is changed as follows. In this case, the structure of the parts other than the operation section 33 are the same as the treating instrument 31 of the second embodiment. The same reference numerals are added to the portions common to the second embodiment, and the explanation is omitted.

More specifically, thin layers 131a and 131b are formed on the lower side portions of the fixed handle 51 and the movable handle 52, respectively. The layers 131a and 131b are formed to be thinner than the upper side portions of the fixed handle 51 and the movable handle 52. Then, elastic members (finger load reducing means) 132a and 132b are formed to cover the outer surfaces of the thin layers 131a and 131b. In this case, the thin layer 131a of the fixed handle 51 is positioned on the ring of the finger inserting section 54 of the fixed handle 51 and a portion close to the ring. The thin layer 131b of the movable handle 52 is positioned on the ring of the finger inserting section 56 of the fixed handle 52 and a portion close to the ring. The respective elastic members 132a and 132b are formed on the entire outer surfaces of the respective thin layers 131a and 131b of the fixed handle 51 and the movable handle 52 by insert molding.

According to the above-explained structure, the elastic members 132a and 132b are mounted on not only the inside of the finger inserting sections 54 and 56 but also the outside of the ring and the entire outer surfaces close thereto. In a case where the fingers, which are not inserted into the rings of the finger inserting sections 54 and 56, e.g., the ring finger (third finger) is inserted into the ring of the finger inserting section 54, there can be obtained an advantage in which the operator feels the pain in the middle finger (second finger) and the little finger (fourth finger), which are positioned on the outside of the finger inserting section 54. As a result, the operator's fatigue and pain can be reduced.

Figures 15A, 15B, 15C:
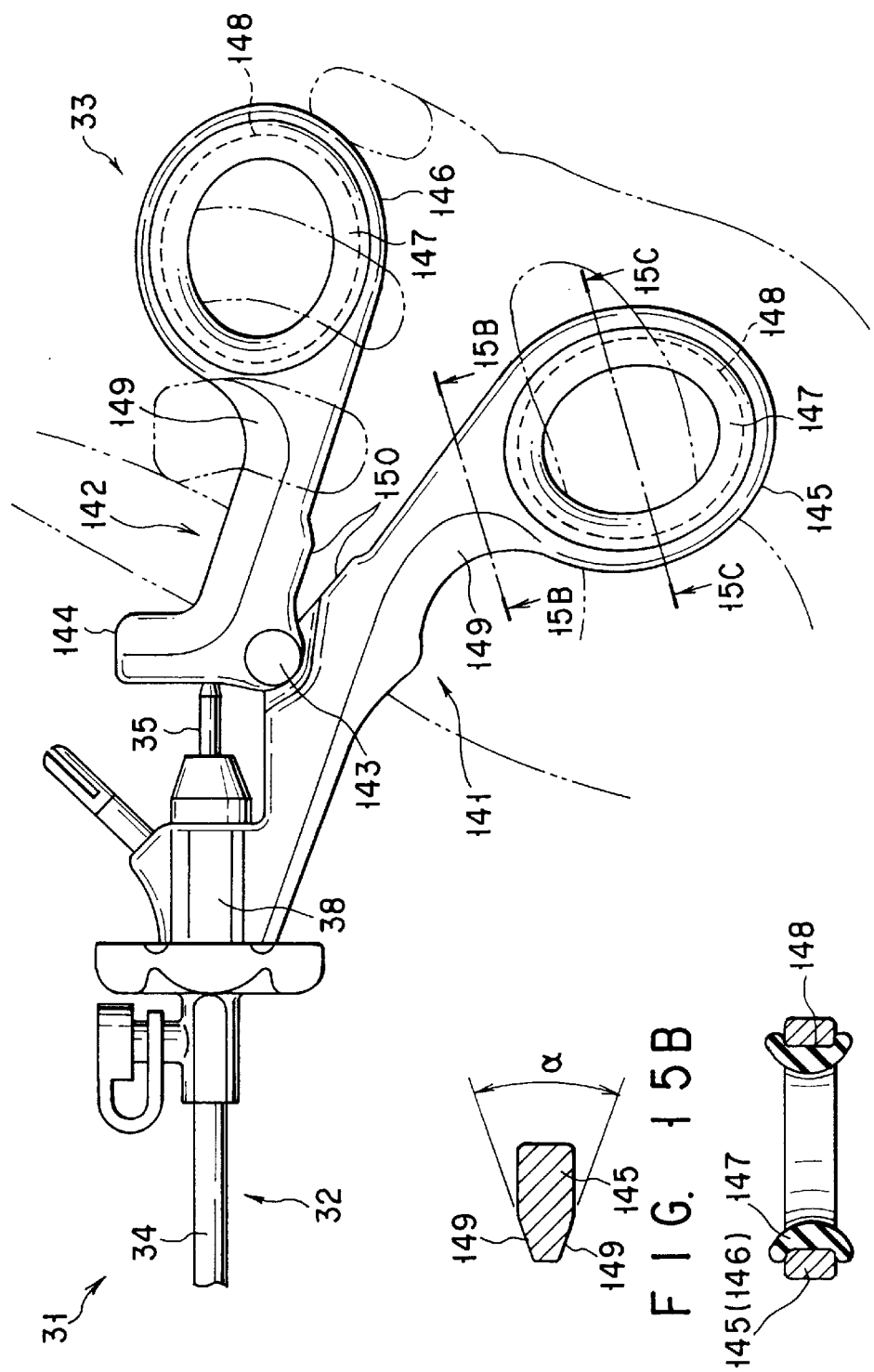
FIG. 15A is a plane view of an operation section showing a ninth modification of the second embodiment.
FIG. 15B is a cross-sectional view cut along a line 15B—15B of FIG. 15A.
FIG. 15C is a cross-sectional view cut along a line 15C—15C of FIG. 15A.
Figure 16:
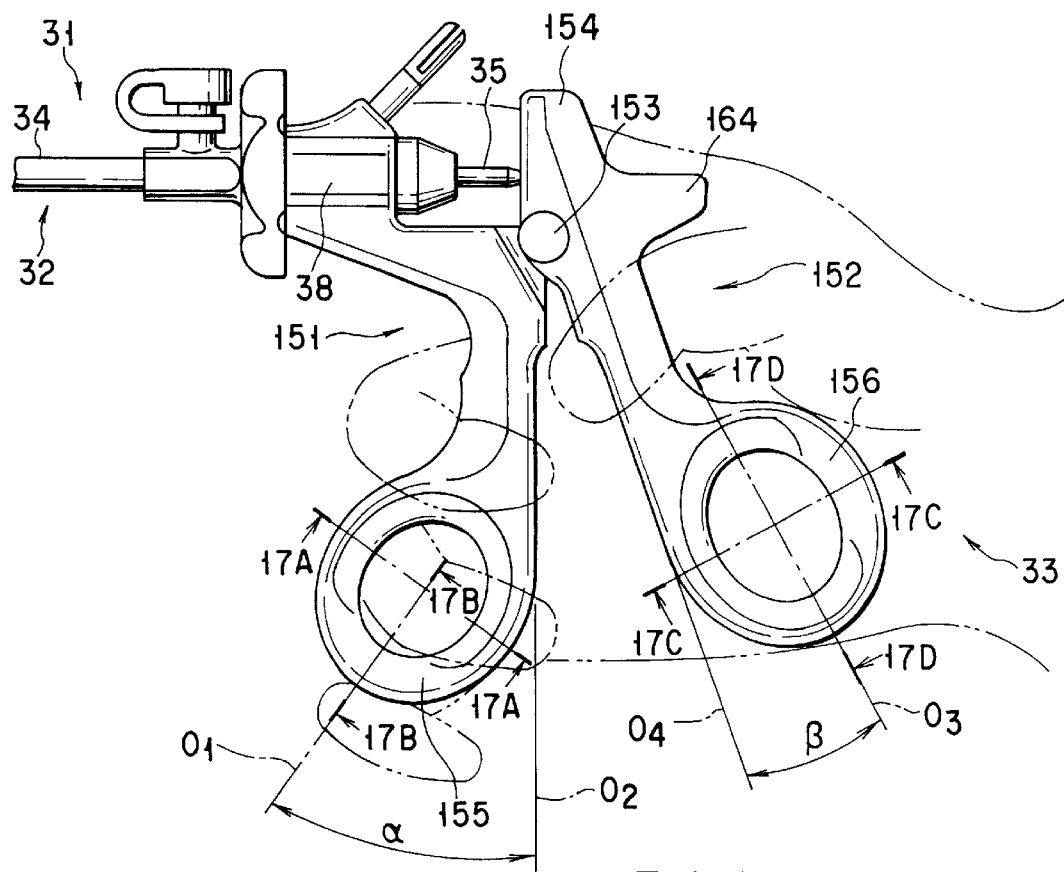
FIG. 16 is a plane view of an operation section showing a tenth modification of the second embodiment.

FIGS. 15A to 15C show a ninth modification of the treating instrument 31 of the second embodiment (FIGS. 2A and 2B). In this modification, the structure of the operation section 33 of the first modification (FIGS. 3A and 3B) is changed as follows. In this case, the structure of the parts other than the operation section 33 are the same as the treating instrument 31 of the second embodiment. The same reference numerals are added to the portions common to the second embodiment, and the explanation is omitted.

The operation section 33 of the treating instrument 31 of this modification has a fixed handle 141 whose angle of bend to the axis of the insertion section 32 is smaller than the fixed handle 51 of the first modification. A movable handle 142 is coupled to the fixed handle 141 to be freely rotatable by a supporting member 143. The base portion of the drive shaft 35 is coupled to a head portion 144 of the movable handle 142.

A ring-shaped finger inserting section 145 is formed at the end portion of the fixed handle 141. Similarly, a ring-shaped finger inserting section 146 is formed at the end portion of the fixed handle 142. An elastic ring 147 is formed on the entire inner peripheral surface of each of the finger inserting sections 145 and 146 to be detachable or to be as one body. In this case, as shown in FIG. 15C, a concave engaging groove 148 is formed on the outer peripheral surface of each elastic ring 147. Then, the engaging groove 148 of each elastic ring 147 is engaged with the inner peripheral surface of each of the finger inserting sections 145 and 146. Under such a state, the elastic ring 147 is fixed to each of the finger inserting sections 145 and 146.

Moreover, as shown in FIG. 15B, tapered inclination surfaces 149 are symmetrically formed at the portion close to the finger inserting section 145 of the fixed handle 141. Similarly, the inclination surfaces 149 are symmetrically formed at the portion close to the finger inserting section 146 of the movable handle 142. In this modification, an opening angle α between right and left inclination surfaces 149 is set to about 40°.

Moreover, at the center of the supporting member 143 in the fixed handle 141 and the movable handle 142, there is formed an abutting portion 150 for restricting the movable range of the movable handle 142 to the closing direction.

According to the above-mentioned structure, at the time of using the treating instrument 31, the operator inserts his thumb into the ring of the finger inserting section 146 of the movable handle 142. Also, the operator inserts his ring finger into the ring of the finger inserting section 145 of the fixed handle 141. Under such a state, the inclination surface 149 of the fixed handle 141 is formed to be fitted to the operator's middle finger.

In this case, the similar inclination surface 149 is provided in the movable handle 142. Due to this, the operator shifts his grip on the treating instrument 31. Then, as shown by the imaginary line of FIG. 15A, the operator inserts his thumb into the ring of the finger inserting section 145 of the fixed handle 141. Also, the operator inserts his ring finger into the ring of the finger inserting section 146 of the movable handle 142. Even under such a state, the inclination surface 149 of the fixed handle 142 can be fitted to the operator's middle finger.

Moreover, since the inclination surfaces 149 are symmetrically formed, the same operability can be obtained even if the operator operates the treating instrument 31 with either hand. As a result, even in a case where the operator shifts his grip on the treating instrument 31, the operator does not have a pain in his fingers. Therefore, there can be obtained an advantage in which the operator's fatigue and pain can be reduced.

FIGS. 16, and 17A to 17D show a tenth modification of the treating instrument 31 of the second embodiment (FIGS. 2A and 2B). In this modification, the structure of the operation section 33 of the first modification (FIGS. 3A and 3B) is changed as follows. In this case, the structure of the parts other than the operation section 33 are the same as the treating instrument 31 of the second embodiment. The same reference numerals are added to the portions common to the second embodiment, and the explanation is omitted.

More specifically, in the operation section 33 of the treating instrument 31 of this modification, there is provided a fixed handle 151, which is bent to be substantially perpendicular to the central axis of the insertion section 32. A movable handle 152 is coupled to the fixed handle 151 to be freely rotatable by a supporting member 153. The base end portion of the drive shaft 35 is coupled to a head portion 154 of the movable handle 152.

Moreover, a ring-shaped finger inserting section 155 is provided on the end portion of the fixed handle 151. Moreover, a ring-shaped finger inserting section 156 is provided on the end portion of the movable handle 152.

In this modification, an opening angle α between a central axis $O_1$ of the ring of the finger inserting section 155 and a central axis $O_2$ of the fixed handle 151 in the bending direction to the central axis of the insertion section 32 is set to about 36°. Moreover, an opening angle β between a central axis $O_3$ of the ring of the finger inserting section 156 and a central axis $O_4$ of the movable handle 152 is set to about 9°.

Figure 17A:
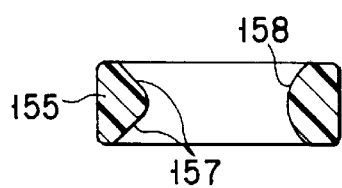
FIG. 17A is a cross-sectional view cut along a line 17A—17A of FIG. 16.
Figure 17B:
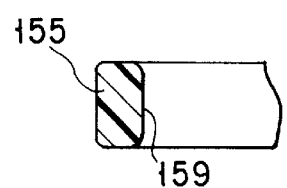
FIG. 17B is a cross-sectional view cut along a line 17B—17B of FIG. 16.
Figure 17C:
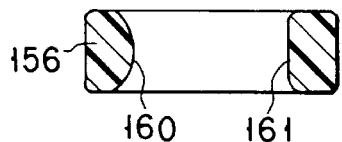
FIG. 17C is a cross-sectional view cut along a line 17C—17C of FIG. 16.
Figure 17D:
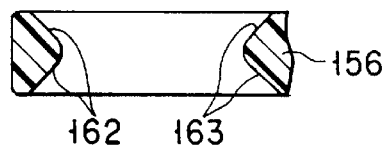
FIG. 17D is a cross-sectional view cut along a line 17D—17D of FIG. 16.

Moreover, on the inner peripheral surface of the finger inserting section 155 of the fixed handle 151, two inclination surfaces 157, a circular surface 158, and a plane surface 159 are smoothly formed. The inclination surfaces 157 are placed at the left end side of FIG. 17A, which is a cross-section cut along lines A—A of FIG. 16, to have a substantially V-shaped cross-section. The circular surface 158 is placed at the right end side of FIG. 17A to have a substantially semi-circular cross-section. The plane surface 159 is shown in FIG. 17B, which is a cross-section cut along lines B—B of FIG. 16.

Furthermore, on the inner peripheral surface of the finger inserting section 156 of the movable handle 152, a circular surface 160, a plane surface 161, two inclination surfaces 162, and two inclination surfaces 163 are smoothly formed. The circular surface 160 is placed at the left end side of FIG. 17A, which is a cross-section cut along lines C—C of FIG. 16, to have a substantially semi-circular cross-section. The plane surface 161 is placed at the right end side of FIG. 17A. The inclination surfaces 162 are placed at the left end side of FIG. 17D, which is a cross-section cut along lines D—D of FIG. 16, to have a substantially V-shaped cross-section. The inclination surfaces 163 are placed at the right end side of FIG. 17D to have a substantially V-shaped cross-section.

The inner peripheral shape of the ring of each of the finger inserting sections 155 and 156 is symmetrical. Also, at the portion close to the supporting member 153 of the movable handle 152, a projecting portion 164 is formed toward the outside.

Then, in a case where the operator holds the operation section 33 at the time of using the treating instrument 31, the fingers, which are inserted to the rings of the finger inserting sections 155 and 156, come in contact with the inclination surfaces 157 of the ring of the finger inserting section 155, the circular surface 158, and the inclination surfaces 162 and 163 of the finger inserting section 156, respectively.

In opening the movable handle 152 to the fixed handle 151, the back and side portions of the fingers inserted into the finger inserting sections 155 and 156 come in contact with the plane 159 of the ring of the finger inserting section 155 and the plane 161 of the finger inserting section 156, respectively.

In closing the movable handle 152 to the fixed handle 151, the belly portions of the fingers inserted into the finger inserting sections 155 and 156 come in contact with the circular surface 158 of the ring of the finger inserting section 155 and the circular surface 160 of the ring of the finger inserting section 156, respectively.

According to the above-mentioned structure, even in a case where the operator performs the opening/closing operation of the movable handle 152 to the fixed handle 151 and holds the operation section 33 with either hand, the contact area between the fingers and the rings of the respective finger inserting sections 155 and 156 can be sufficiently largely ensured. As a result, there can be obtained an advantage in which the operator does not have a pain in his fingers.

Moreover, as explained above, the projecting portion 164 is formed toward the outside is formed at the portion close to the supporting member 153 of the movable handle 152. As a result, this structure can be dealt with the case in which the operator's thumb is off the ring of the finger inserting section 156 of the movable handle 152 as shown by the imaginary line of FIG. 16.

Figure 18:
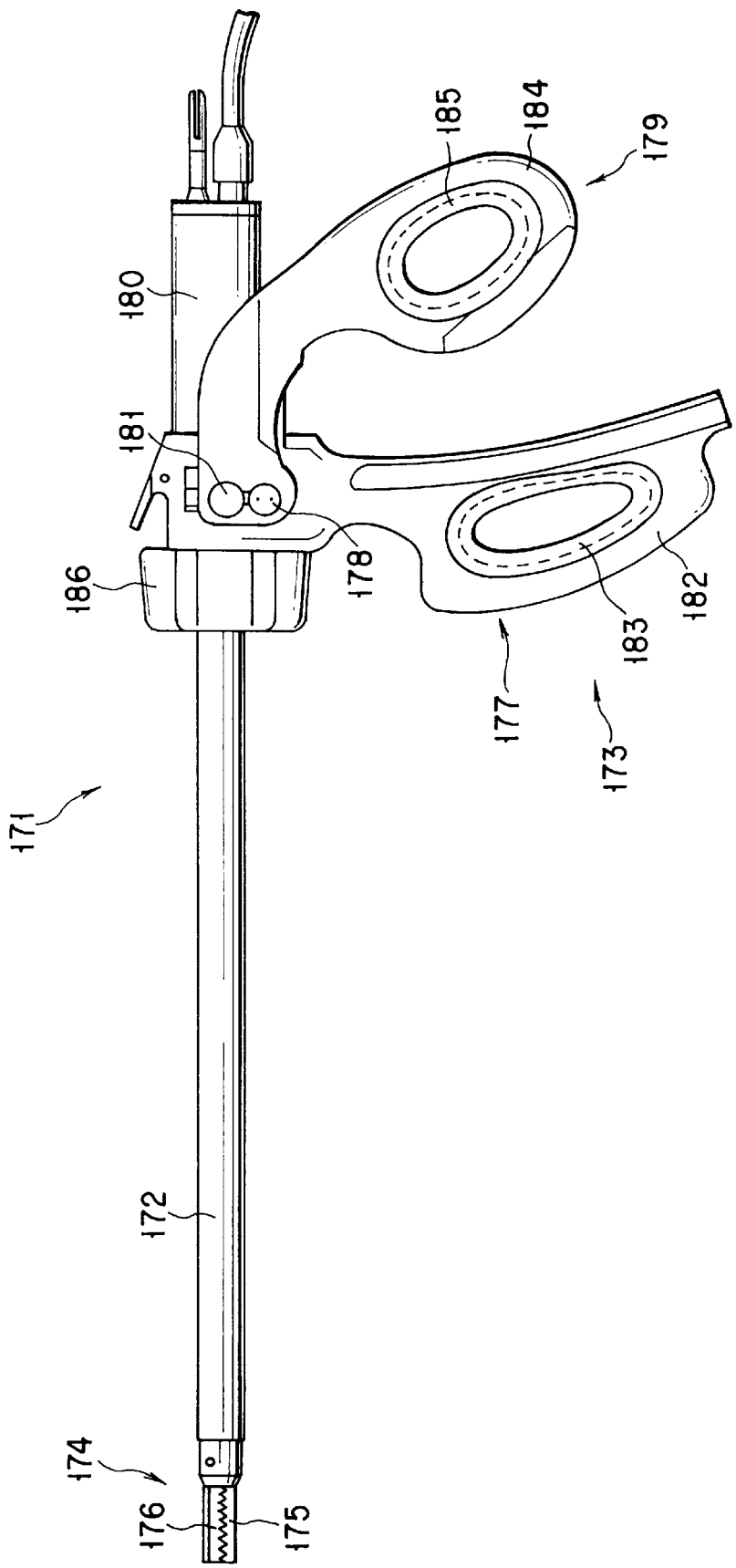
FIG. 18 is a side view showing a treating instrument for an operation of a third embodiment of the present invention.

FIG. 18 shows a third embodiment of the present invention, which is applied to an ultrasonic probe 171. The ultrasonic probe 171 has a thin and long insertion section 172, which is inserted to a living body through a trocar sheath (not shown), and an operation section 173, which is coupled to the base end portion of the insertion section 172.

Moreover, a top end treating section 174 is provided at the top end of the insertion section 172. The top end treating section 174 has a fixed gear 175 and a movable gear 176. The base end portion of the movable gear 176 is coupled to the top end portion of the insertion section 172 to be rotatable.

The operation section 173 has a fixed handle 177 and a movable handle 179, which is connected to the fixed handle 177 by a supporting member 178, to be freely rotatable. Also, an ultrasonic oscillator 180 is provided at the rear end of the upper portion of the fixed handle 177. Then, ultrasonic oscillation generated from the ultrasonic oscillator 180 is transmitted to the top end treating section 174 of the ultrasonic probe 171 through an oscillation transmission member (not shown) provided in the insertion section 172.

In the insertion section 172, a drive shaft (not shown) for driving the movable gear 176 is provided. A drive shaft connecting section 181, which is fixed to the upper end portion of the movable handle 179, is coupled to the base end portion of the drive shaft. Then, in accordance with the opening and closing operation of the movable handle 179 in which the movable handle 179 is rotated around the supporting member 178 to the fixed handle 177, the drive shaft is axially advanced and retreated in the insertion section 172 through the drive shaft connecting section 181. In accordance with the operation of the drive shaft, the movable gear 176 is opened/closed to the fixed gear 175.

A substantially long hole-shaped finger inserting section 182 is formed at the lower portion of the fixed handle 177. An elastic ring 183 is formed at the inside of the finger inserting section 182 to be freely detachable or as one body.

Moreover, a substantially elliptic finger inserting section 184 is formed at the lower portion of the movable handle 179. An elastic ring 185 is formed at the inside of the finger inserting section 184 to be freely detachable or as one body.

A rotation operation knob 186 is formed on a coupling portion of the inserting section 172 and the operation section 173. By the operation of the rotation operation knob 186, the inserting section 172 is axially rotated to the operation section 173.

The following will explain a function of the above-mentioned structure.

Specifically, at the time of using the treating instrument 31, the movable handle 179 is operated. Thereby, the drive shaft of the inserting section 172 is moved back and forth through the drive shaft connecting section 181, and the movable gear 176 is opened and closed to the fixed gear 175.

Furthermore, ultrasonic oscillation generated from the ultrasonic oscillator 180 is transmitted to the top end treating section 174 of the ultrasonic probe 171 through the oscillation transmission member (not shown) provided in the insertion section 172. In other words, the movable handle 179 is operated to hold the tissue of the living body (not shown) between the movable gear 176 and the fixed gear 175. In such a state, ultrasonic oscillation generated from the ultrasonic oscillator 180 is transmitted to the top end treating section 174 of the ultrasonic probe 171. Thereby, the tissue of the living body held between the movable gear 176 and the fixed gear 175 can be treated.

According to the above-explained structure, elastic rings 183 and 185, which are formed of elastic material, are inserted into the finger inserting sections 182 and 184, respectively. As a result, similar to the first modification of the second embodiment, the operator does not have a pain in his fingers, which are inserted into the finger inserting sections 182 and 184, during the operation even for a long period of time. Therefore, there can be obtained an advantage in which the operator's fatigue and pain can be reduced.

Figure 19:
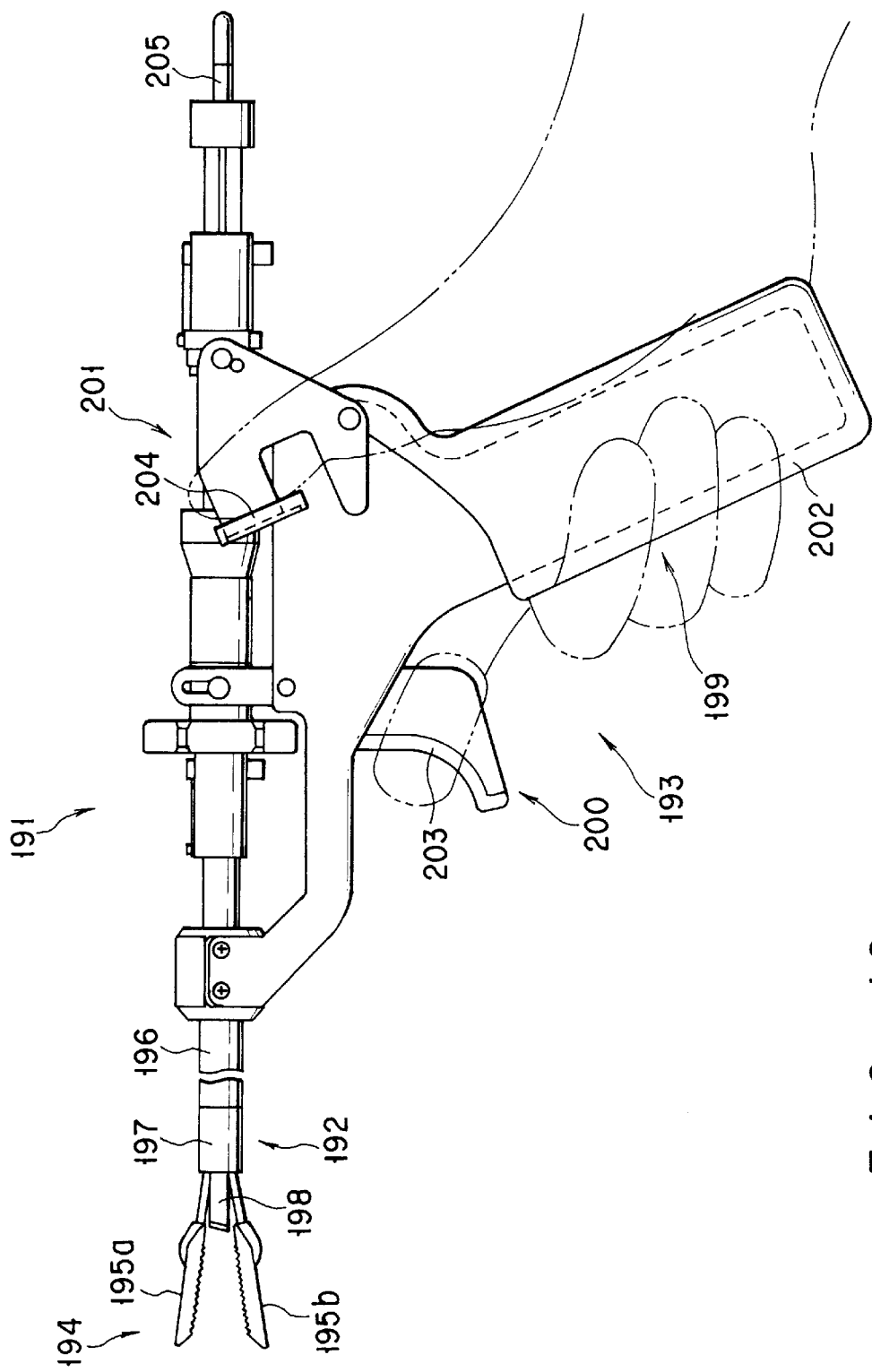
FIG. 19 is a side view showing a treating instrument for an operation of a fourth embodiment of the present invention.

FIG. 19 shows a fourth embodiment of the present invention. In a treating instrument 191 of this embodiment, there are provided a thin and long inserting section 192 and an operation section 193 coupled to the base end portion of the inserting section 192.

A top end treating section 194 is provided at the top end side of the inserting section 192. The top end treating section 194 has a pair of holding members 195a and 195b. Moreover, the inserting section 192 has a fixed sheath 196 and a movable sheath 197, which is axially movable to the fixed sheath 196. A knife 198 is provided at the top end portion of the movable sheath 197.

The operation section 193 has a holding section 199, which is holed by the operator's hand, a trigger section 200 connected to the movable sheath 197, and a knife lever 201 connected to the knife 198.

As shown in FIG. 19, elastic members 202, 203, and 204 are provided on the portions contacting the operator's hand. Each of the elastic members 202, 202, and 204 is formed to be freely detachable or as one body.

The holding members 195a and 195b are insulated from each other. Each of the holding members 195a and 195b has two high frequency connection pins 205 on the rear end side of the operation section 193 to supply a high frequency current to the holding members 195a and 195b.

At the time of using the treating instrument 191 of this embodiment, as shown by an imaginary line of FIG. 19, the operator holds the holding section 199 of the operation section 193. In this state, the trigger 200 is pulled toward the operator. As a result, the movable sheath 197 is moved to the top end side, and the holding members 195a and 195b are closed to hold the tissue of the living body (not shown).

At this time, the high frequency current is supplied to the holding members 195a and 195b through the high frequency connection pins 205. Thereby, the tissue of the living body held by the holding members 195a and 195b is burned. Also, the knife lever 201 is rotated to move the knife 198 to the top end side. Thereby, the tissue of the living body held by the holding members 195a and 195b is cut.

Thus, according to the above-explained structure, elastic members 202, 203, and 204 are provided on the portions contacting the operator's hand. As a result, at the time of using the treating instrument 191 of this embodiment, the operator does not have a pain in the portions such as operator's fingers and palm which contact the holding section 199, the trigger 200, and the knife lever 201. Moreover, the operator's fatigue and pain in his fingers and hand can be reduced.

The elastic members 202, 203, and 204 serve as a stopper for the operator's fingers and palm. As a result, there can be obtained an advantage in which the maintenance of the operation section 193 and the reliability can be improved.

Figure 20:
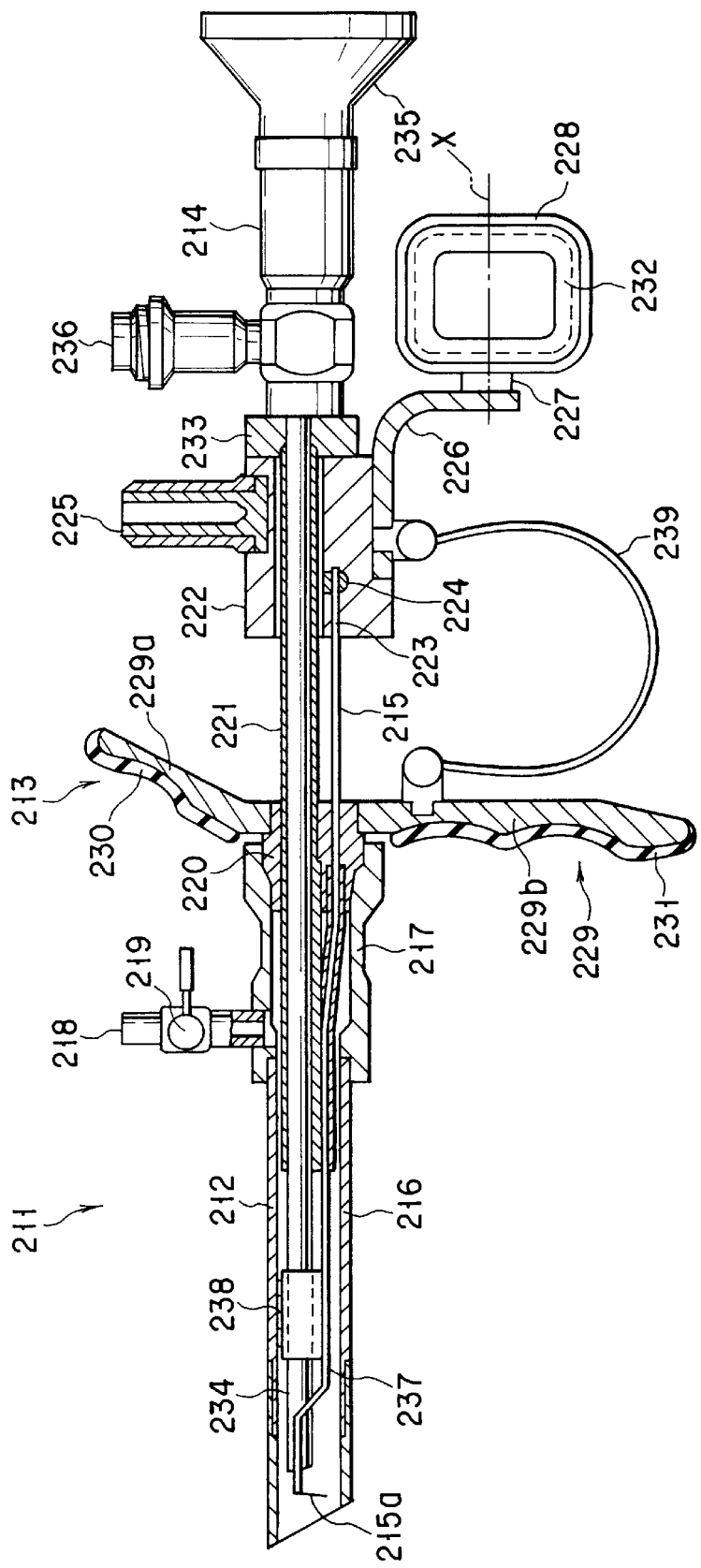
FIG. 20 is a vertical cross-sectional view showing a treating instrument for an operation of a fifth embodiment of the present invention.

FIG. 20 shows a fifth embodiment of the present invention, which is applied to a resectoscope 211. The resectoscope scope 211 comprises a thin tubular sheath 212, an operation section 213 provided at the rear end of the sheath 212, an optical scope 214 inserted into the sheath 212 from the operation section 213, and an electrode device 215.

A loop top end electrode 215a, serving as an electrical current conduction, is provided at the top end portion of the electrode device 215.

The sheath has an inserting section 216, which is inserted into a body cavity from the urethra, and a main body 217 connected to the rear end of the inserting section 216. Then, a supply port 218 for supplying perfusate to the affected part is provided in the main body 217. A cock 219 for opening and closing is provided in the middle of the supply port 218.

The operation section 213 has an operation section main body 220, which is connected to the rear end of the sheath to be freely detachable. A guide shaft 221 is projected on the rear end of the operation section main body 220. A slider 222 is maintained to be freely slidable on the guide shaft 221.

The slider 222 has a maintaining section 223 for maintaining the electrode device 215 and an electrical current conduction 224 for applying high frequency current to the electrode device 215. The electrical current conduction 224 is connected to a connector 225 provided in the slider 222. A power supply cord of a high frequency power supply unit (not shown) is connected to the connector 225.

One end side of a first handle 226 is fixed to the lower surface of the slider 222. The other end side of the first handle 226 is downwardly bent to be substantially L-shaped. Moreover, on the L-shaped bending portion of the first handle 226, there is provided a ring-shaped finger hooking section 228 for hooking operator's thumb through a spindle 227. The finger hooking section 228 is formed to be freely rotatable about an axis X of FIG. 20.

The operation section main body 220 has a second handle 229. The second handle 229 has an upper portion finger hooking portion 229a of a lever shape and a lower portion finger hooking portion 229b of a lever shape. The upper portion finger hooking portion 229a extends upward, and the lower portion finger hooking portion 229b extends downward. Then, one end portion of a plate spring member 239 of substantially U-shape is fixed to the lower portion finger hooking portion 229b. The other end portion of the plate spring member 239 is fixed to the lower surface of the slider 222 together with the first handle 226. Then, the operator's thumb is inserted to the finger hooking portion 228 of the first handle 226. Then, other fingers are hooked on the upper and lower finger hooking portions 229a and 229b of the second handle 229. In such a state, the operator performs the operation for reducing the distance between the first and second handles 226 and 229 against spring force of the plate spring member 239. Thereby, the slider 222 can be slid forward. Then, the top end electrode 215a of the electrode device 215 is projected from the top end of the sheath 212.

In the upper and lower finger hooking portions 229a and 229b of the operation section 213 and the finger hooking portion 228 of the slider 222, the elastic members 230, 231 and 232 are provided to the portions contacting the operator's fingers to be freely detachable or as one body.

A stopper 233 is provided on the rear end portion of the guide shaft 221. The stopper 233 prevents the slider 222 from being detached from the guide shaft 221. The interior of the guide shaft 221 is hollow, and the optical scope 214 is inserted into the sheath 212 through the guide shaft 221.

The optical scope 214 has an insertion section 234, which is inserted into the sheath 212, and an eyepiece section 235, which is provided on the rear end of the inserting section 234. In the vicinity of the eyepiece section 235, a light guide connector 236 is provided.

The electrode device 215 has an electrical conduction member (wire) (not shown) for electrically applying the high frequency current to the top end electrode 215a, and an insulating member 237 for insulating the electrical conduction member. The electrode device 215 also has a stabilizer 238 for positioning the top end portion of the optical scope 214 to the center of the top end electrode 215a.

At the time of using the resectoscope 211 of this embodiment, the sheath 212 is inserted into the body cavity from the urethra. Sequentially, the operator hooks his fingers on the upper and lower finger hooking portions 229a and 229b of the second handle 229 and the finger hooking portion 228 of the first handle 226 as observing the body cavity by the optical scope 214, so that the slider 222 is slid forward. Thereby, the top end electrode 215a of the electrode device 215 is projected from the top end of the sheath 212. At this time, the high frequency current is applied to the top end electrode 215a through the connector 236, and the conduction member (wire) (not shown). Thereby, the affected part, which contacts the top end electrode 215a, e.g., enlarged prostate can be cut off.

Thus, according to the above-explained structure, the elastic members 230, 231, and 232 are provided on the portions contacting the operator's fingers of the upper and lower finger hooking portions 229a and 229b of the operation section 213 and the finger hooking portion 228 of the slider 222. As a result, the operator's fingers can be brought in contact with the elastic members 230, 231, 232 when the operator operates the upper and lower finger hooking portions 229a and 229b of the operation section 213 and the finger hooking portion 228 of the slider 222. In other words, the operator's fingers are not directly brought in contact with the upper and lower finger hooking portions 229a and 229b of the operation section 213 and the finger hooking portion 228 of the slider 222. As a result, the operator does not have a pain in his fingers contacting the upper and lower finger hooking portions 229a and 229b of the operation section 213 and the finger hooking portion 228 of the slider 222. Therefore, the operator's fatigue and pain in his fingers can be reduced. Moreover, since the elastic members 230, 231, and 232 serve as a stopper for the operator's fingers, there can be obtained an advantage in which the maintenance of the operation section 213 and the reliability can be improved.

Figure 21:
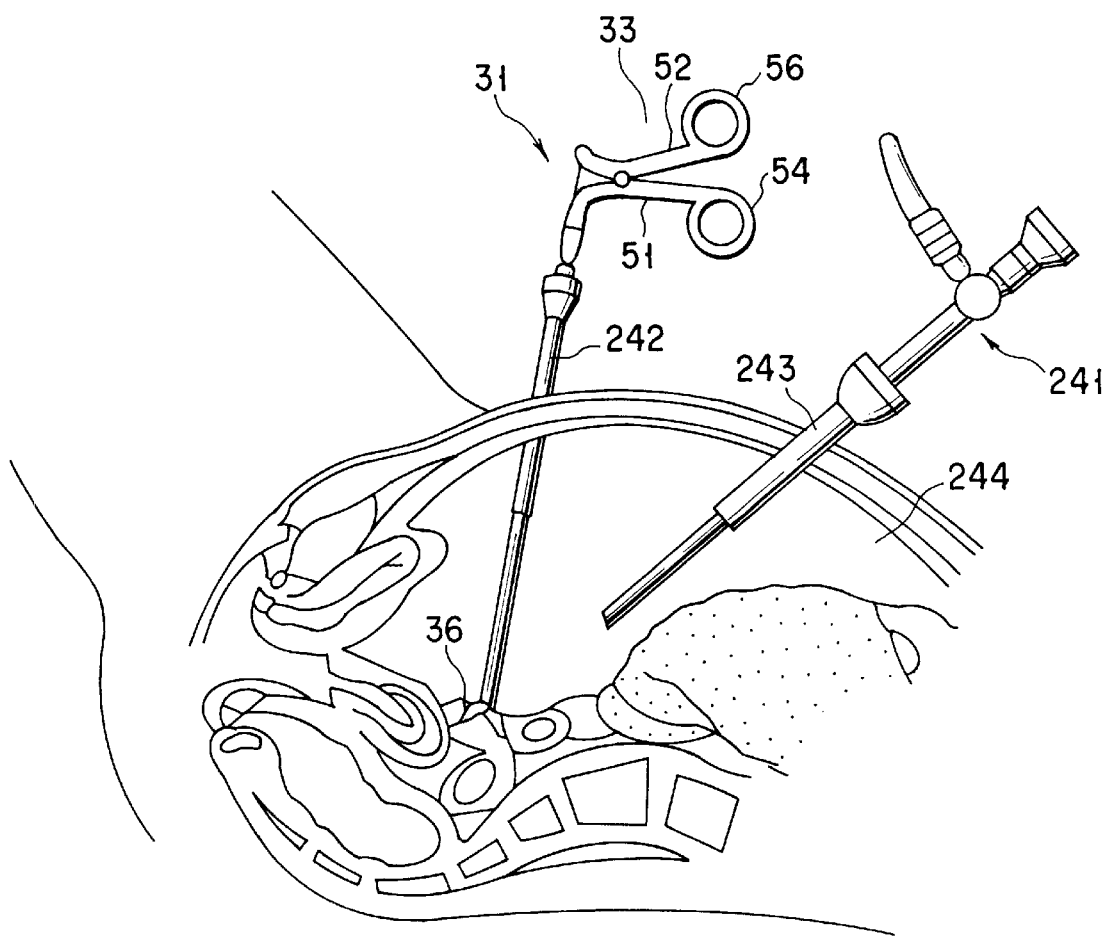
FIG. 21 is a structural view showing a treatment state in which a treating instrument for an operation of a sixth embodiment of the present invention is combined with an endoscope.
Figures 22A, 22B:
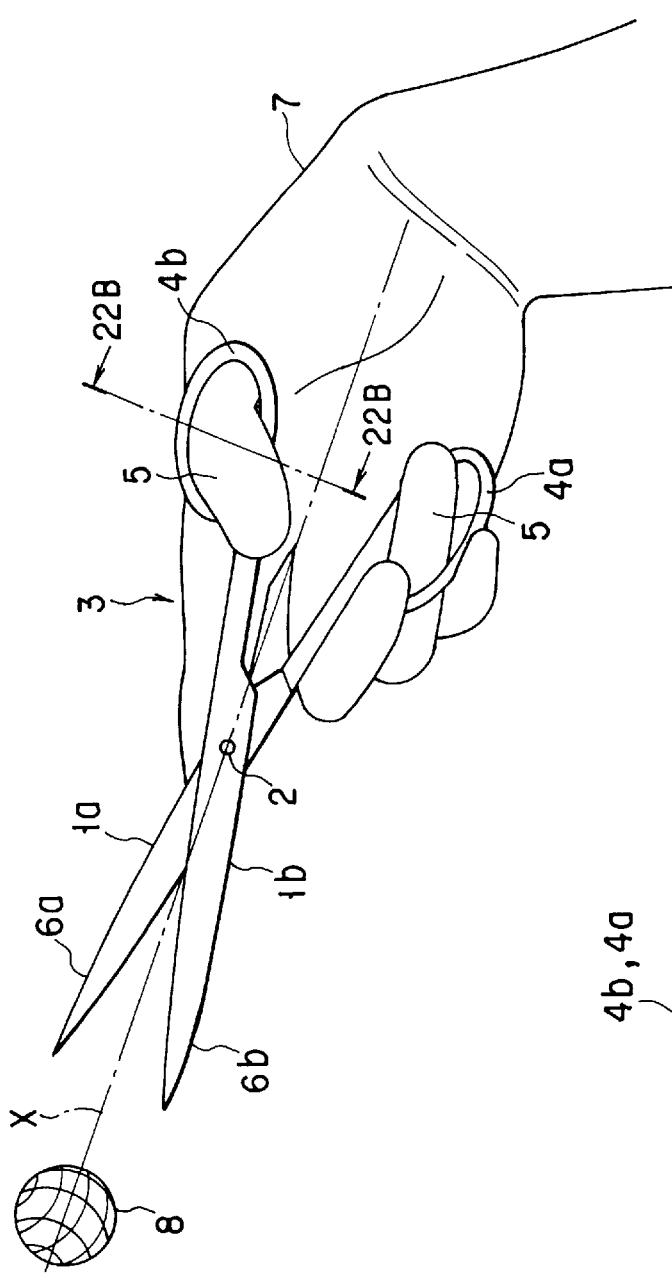
FIG. 22A is a side view showing the using state of the conventional surgical scissors.
FIG. 22B is a cross-sectional view cut along a line of 22B—22B of FIG. 22A.

FIG. 21 shows a sixth embodiment of the present invention. In this embodiment, the treating instrument 32 shown in FIGS. 3A and 3B is combined with an endoscope 241. In this case, hollow tubular-typed trocar sheathes 242 and 243 are passed into patient's skin and fascia in advance, and the top end of each trocar sheathes 242 and 243 is inserted to a body cavity 244.

The operator inserts the treating instrument 31 and the top end portion of the endoscope 241 through the hollow portions of the trocar sheathes 242 and 243 from the patient's body cavity 244 as shown in FIG. 21. Under this state, the operator operates the operation section 33 of the treating instrument 31 as observing the body cavity 244 with the endoscope 241 so as to drive the treating section 36. Thereby, the tissue of the body cavity can be treated.

Additional advantages and modifications will readily occur to those skilled in the art. Therefore the invention in its broader aspects is not limited to the specific details and representative embodiments shown and described herein. Accordingly, various modifications may be made without departing from the spirit or scope of the general inventive concept as defined by the appended claims and their equivalents.

We claim:

1. A treating instrument for an operation comprising:
   a main body;
   an operation section provided on a base end portion of said main body, said operation section including a first handle including first finger contacting means for contacting a first one of an operator's finger, a second handle including second finger contacting means for contacting at least a second one of the operator's fingers, and coupling means for coupling said first and second handles to be relatively movable;
   a treating section provided on a top end portion of said main body, said treating section including a movable element which is operable in response to a relative moving operation between said first and second handles; and
   load reducing means for reducing a load on the operator's fingers contacting said first and second finger contacting means, said load reducing means being provided on a section of at least one of said first and second finger contacting means which contacts the operator's fingers;
   wherein said load reducing means comprises an elastic contacting member which is provided to be freely detachable from at least one of said first and second finger contacting means.

2. The treating instrument according to claim 1, wherein said coupling means comprises a rotation support for coupling said first handle and said second handle to be relatively rotatable.

3. The treating instrument according to claim 1, wherein said coupling means includes coupling portions for coupling said first handle and said second handle to be relatively slidable along an axial direction of said main body of said treating instrument.

4. The treating instrument according to claim 1, wherein at least one of said first and second finger contacting means comprises a ring-shaped member through which respective ones of the operator's fingers can be inserted.

5. The treating instrument according to claim 1, wherein said elastic contacting member is formed of silicon rubber.

6. The treating instrument according to claim 1, wherein said contacting member includes a plurality of projections for preventing the operator's fingers from sliding on said contacting member.

7. The treating instrument according to claim 1, wherein said main body of said treating instrument comprises a tubular inserting section for connecting said treating section to said operation section, and a drive shaft, inserted into said inserting section, for transmitting an operation force of said operation section to said treating section.

8. The treating instrument according to claim 1, wherein one of said first and second handles is fixed to said main body of said treating instrument, and the other is supported to be relatively movable with respect to the handle which is fixed to said main body.

9. The treating instrument according to claim 1, wherein at least one of said first and second finger contacting means comprises a ring-shaped member through which respective ones of the operator's fingers can be inserted, said coupling means comprises a rotation support for coupling said first handle and said second handle to be relatively rotatable, and said load reducing means has an inclination surface inclined to a central axis of said ring-shaped member, said inclination surface being formed on at least one part of an inner peripheral surface side of said ring-shaped member.

10. The treating instrument according to claim 9, wherein said ring-shaped member is formed to be rotatable about a center of a rotation shaft provided along an axial direction of one of said first handle and said second handle.

11. The treating instrument according to claim 1, wherein said first and second finger contacting means each comprise a ring-shaped member through which respective ones of the operator's fingers can be inserted, said coupling means comprises a rotation support for coupling said first handle and said second handle to be relatively rotatable, and said load reducing means is provided to place the ring-shaped member of each of said first and second finger contacting means on a plane inclined at an inclination angle of 50 to 70° with respect to a central axis of said main body of said treating instrument.

12. The treating instrument according to claim 11, wherein at least one of the ring-shaped members of said first and second finger contacting means is connected to an end portion of one of said first handle and said second handle so as to be freely rotatable.

13. The treating instrument according to claim 11, wherein the ring-shaped member of at least one of said ring-shaped rings of said first and second finger contacting means comprises an opening portion having a diameter such that a plurality of the operator's fingers can be inserted therethrough.

14. A treating instrument for an operation comprising:

a main body;

an operation section provided on a base end portion of said main body, said operation section including a first handle including first finger contacting means for contacting a first one of an operator's finger, a second handle including second finger contacting means for contacting at least a second one of the operator's fingers, and coupling means for coupling said first and second handles to be relatively movable, a treating section provided on a top end portion of said main body, said treating section including a movable element which is operable in response to a relative moving operation between said first and second handles; and load reducing means for reducing a load on the operator's fingers contacting said first and second finger contacting means, said load reducing means being provided on a section of at least one of said first and second finger contacting means which contacts the operator's fingers;

wherein at least one of said first and second finger contacting means comprises a ring-shaped member through which respective ones of the operator's finger can be inserted, and said load reducing means comprises an elastic contact member formed on at least an inner peripheral surface of said ring-shaped member;

wherein said coupling means comprises a rotation support for coupling said first handle and said second handle to be relatively rotatable;

wherein said main body of said treating instrument comprises a tubular inserting section for connecting said treating section to said operation section, and a drive shaft, inserted into said inserting section, for transmitting an operation force of said operation section to said treating section; and wherein said elastic contacting member of said load reducing means is provided to be freely detachable from said ring-shaped member of said at least one of said first and second finger contacting means.

* * * * *